(12) United States Patent
Wittek

(10) Patent No.: US 6,328,287 B2
(45) Date of Patent: Dec. 11, 2001

(54) METHOD OF SUPPLYING SUBSTANCES TO BE DISPENSED INTO AIR

(76) Inventor: Götz-Ulrich Wittek, 29-30 Warwick Square, London W1 R5RD (GB)

( * ) Notice: Subject to any disclaimer, the term of this patent is extended or adjusted under 35 U.S.C. 154(b) by 0 days.

(21) Appl. No.: 09/842,848

(22) Filed: Apr. 27, 2001

Related U.S. Application Data

(62) Division of application No. 09/983,022, filed on Jun. 8, 1998, now Pat. No. 6,234,455, which is a continuation-in-part of application No. 08/931,456, filed on Sep. 17, 1997, now Pat. No. 5,832,320, which is a continuation of application No. 08/781,028, filed on Jan. 9, 1997, now abandoned, which is a continuation of application No. 08/232,050, filed on Jun. 30, 1994, now abandoned, which is a continuation of application No. PCT/EP96/02925, filed on Mar. 7, 1996.

(30) Foreign Application Priority Data

| Mar. 6, 1995 | (DE) | 196 08 708 |
| Jul. 3, 1995 | (DE) | 195 24 193 |
| Jul. 17, 1995 | (DE) | 195 06 002 |
| Aug. 16, 1995 | (DE) | 195 30 111 |
| Dec. 8, 1995 | (DE) | 195 45 950 |
| Jul. 2, 1996 | (DE) | 196 26 602 |

(51) Int. Cl.$^7$ ............................................ B01F 3/04
(52) U.S. Cl. ................... 261/30; 261/DIG. 65; 261/DIG. 88; 96/222
(58) Field of Search .................. 55/359; 96/222, 96/FOR 175; 261/30, 42, 53, 62, DIG. 17, DIG. 65, DIG. 88

(56) References Cited

U.S. PATENT DOCUMENTS

| 4,528,226 | * | 7/1985 | Sweeny .................... 261/DIG. 88 |
| 4,603,030 | * | 7/1986 | McCarthy .................... 261/30 |
| 4,847,124 | * | 7/1989 | Lux Nee Andrieux ....... 261/DIG. 88 |
| 4,959,087 | * | 9/1990 | Kappernaros .................. 96/222 |
| 5,000,486 | * | 3/1991 | Rua, Jr. et al. .............. 261/DIG. 88 |
| 5,023,020 | * | 6/1991 | Machida et al. ................ 261/30 |
| 5,164,178 | * | 11/1992 | Muysson .................. 261/DIG. 88 |
| 5,167,877 | * | 12/1992 | Pai ............................ 261/30 |
| 5,192,342 | * | 3/1993 | Baron et al. ............... 261/DIG. 88 |
| 5,273,690 | * | 12/1993 | McDowell ................. 261/DIG. 65 |
| 5,565,148 | * | 10/1996 | Pendergrass, Jr. ............. 261/30 |
| 5,695,692 | * | 12/1997 | Kennedy ..................... 261/30 |
| 5,832,320 | * | 11/1998 | Wittek ....................... 396/106 |

* cited by examiner

*Primary Examiner*—C. Scott Bushey
(74) *Attorney, Agent, or Firm*—Burns, Doane, Swecker & Mathis, L.L.P.

(57) ABSTRACT

The invention relates to a device for supplying substances to be dispensed into air or air mixtures, especially scents, with a flat disk-shaped or plate-shaped base body with multiple separate channels running through it essentially parallel to its top and/or bottom sides, with the channels accommodating the substances to be dispensed and containing an inlet port and an outlet port, respectively, so that a stream of gas supplied to the inlet port can flow through it, with the inlet and outlet ports of at least one channel being sealed in a gastight manner until the substance is released and/or the substance is placed with an airtight seal in at least one channel in a reservoir which does not release this is substance until the time of dispensation thereof.

19 Claims, 9 Drawing Sheets

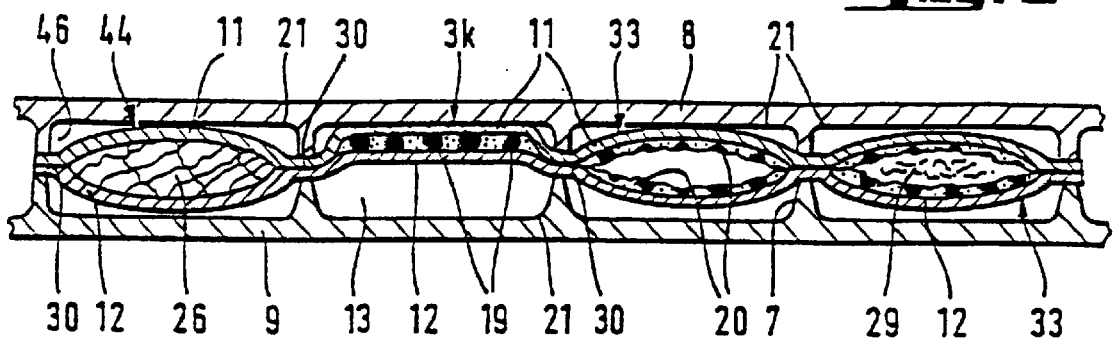
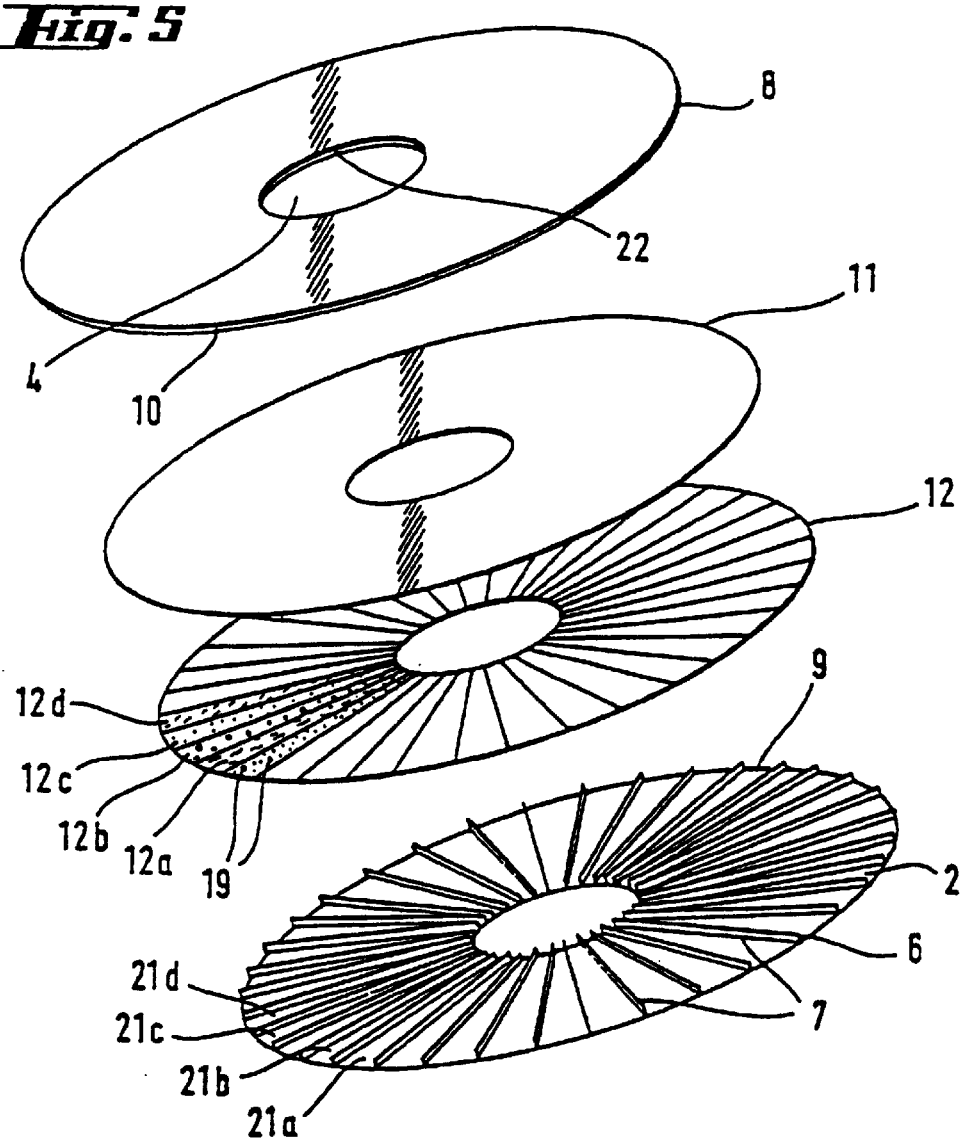

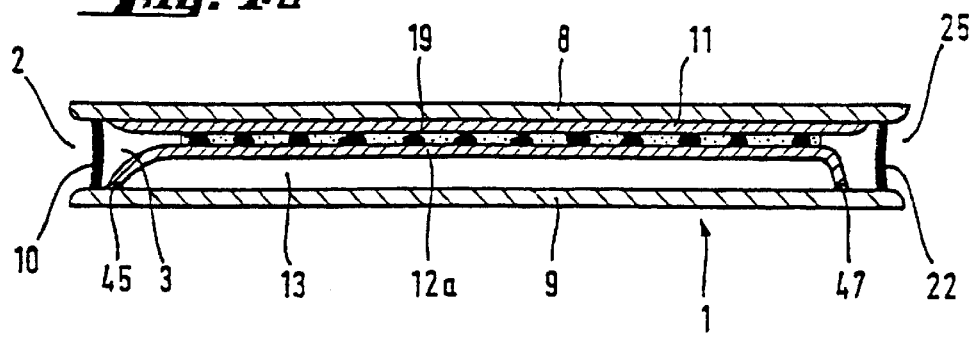
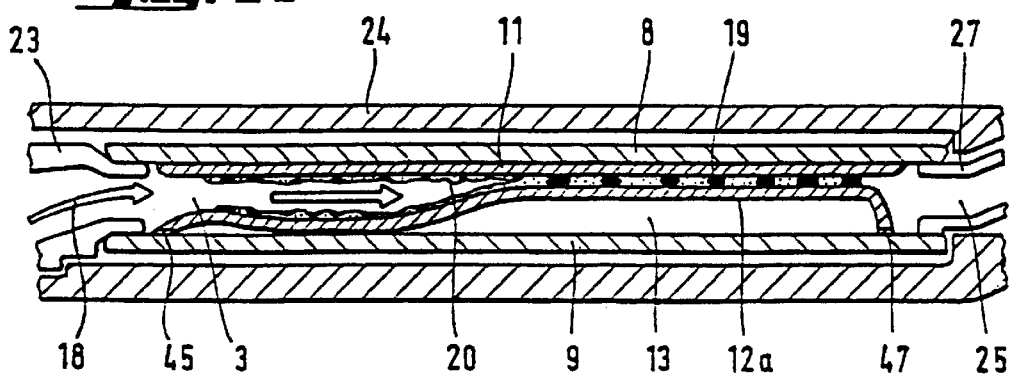
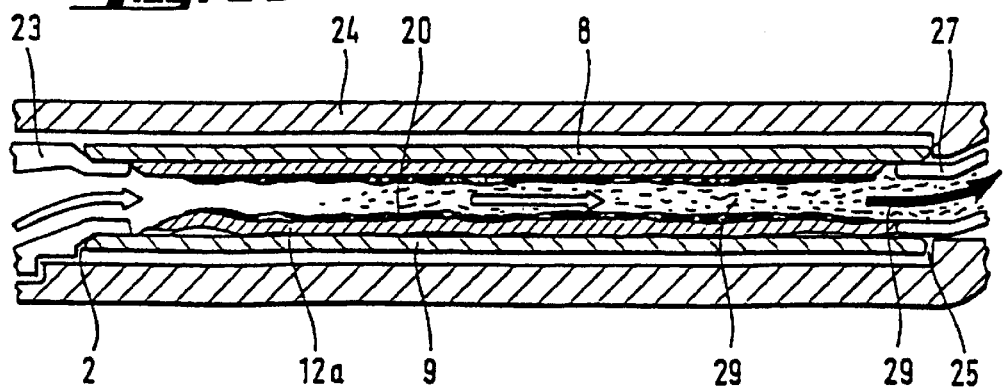

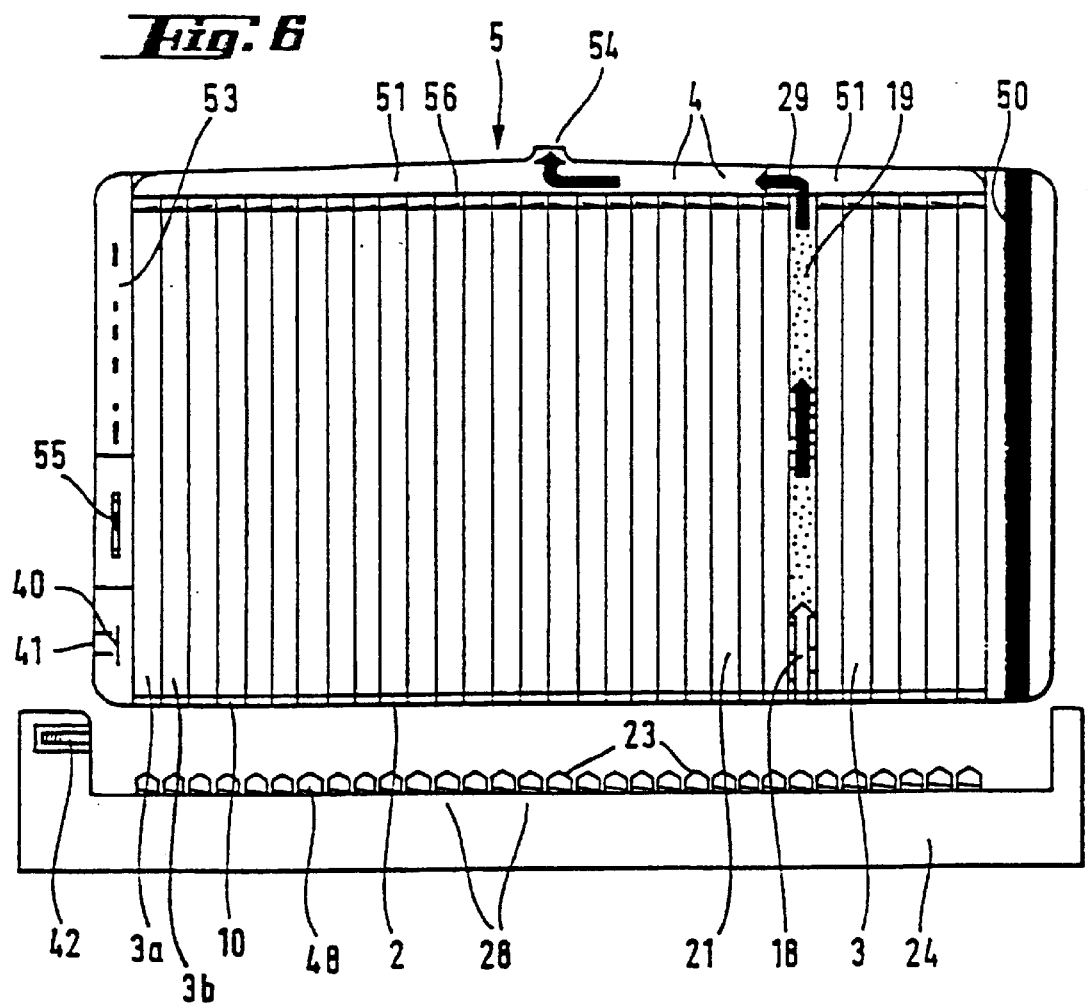
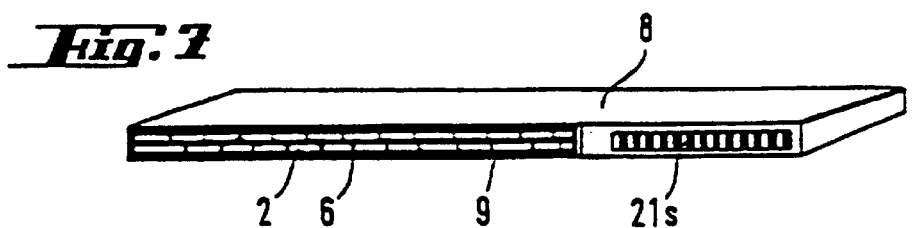
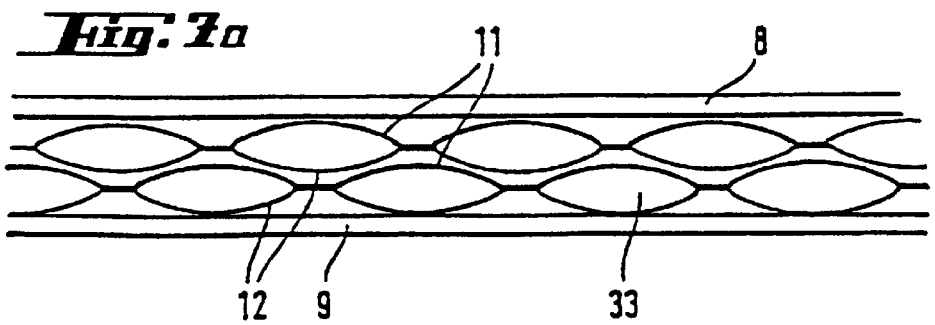

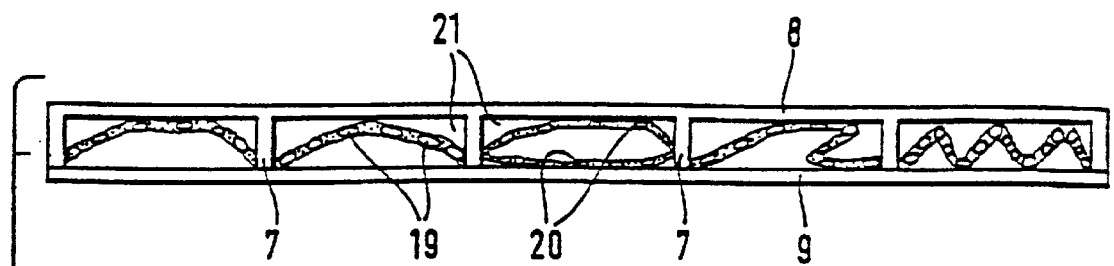
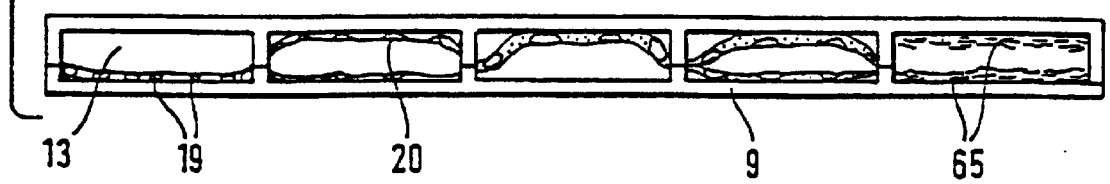
Fig. 8
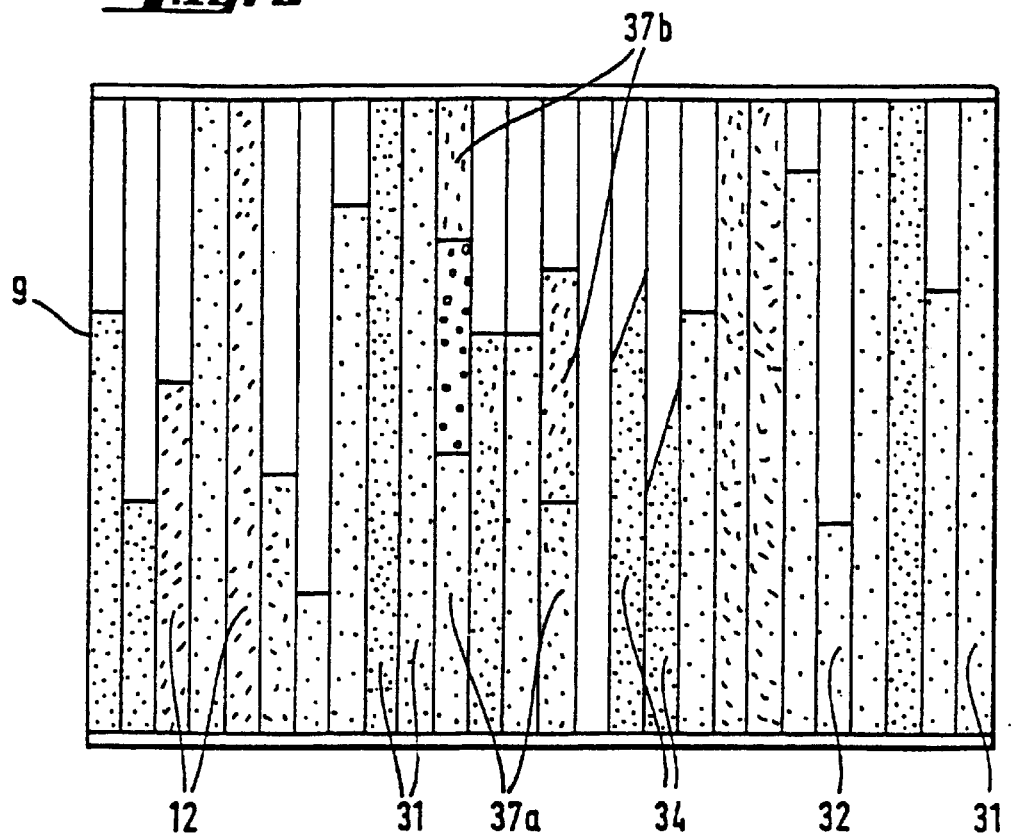
Fig. 9

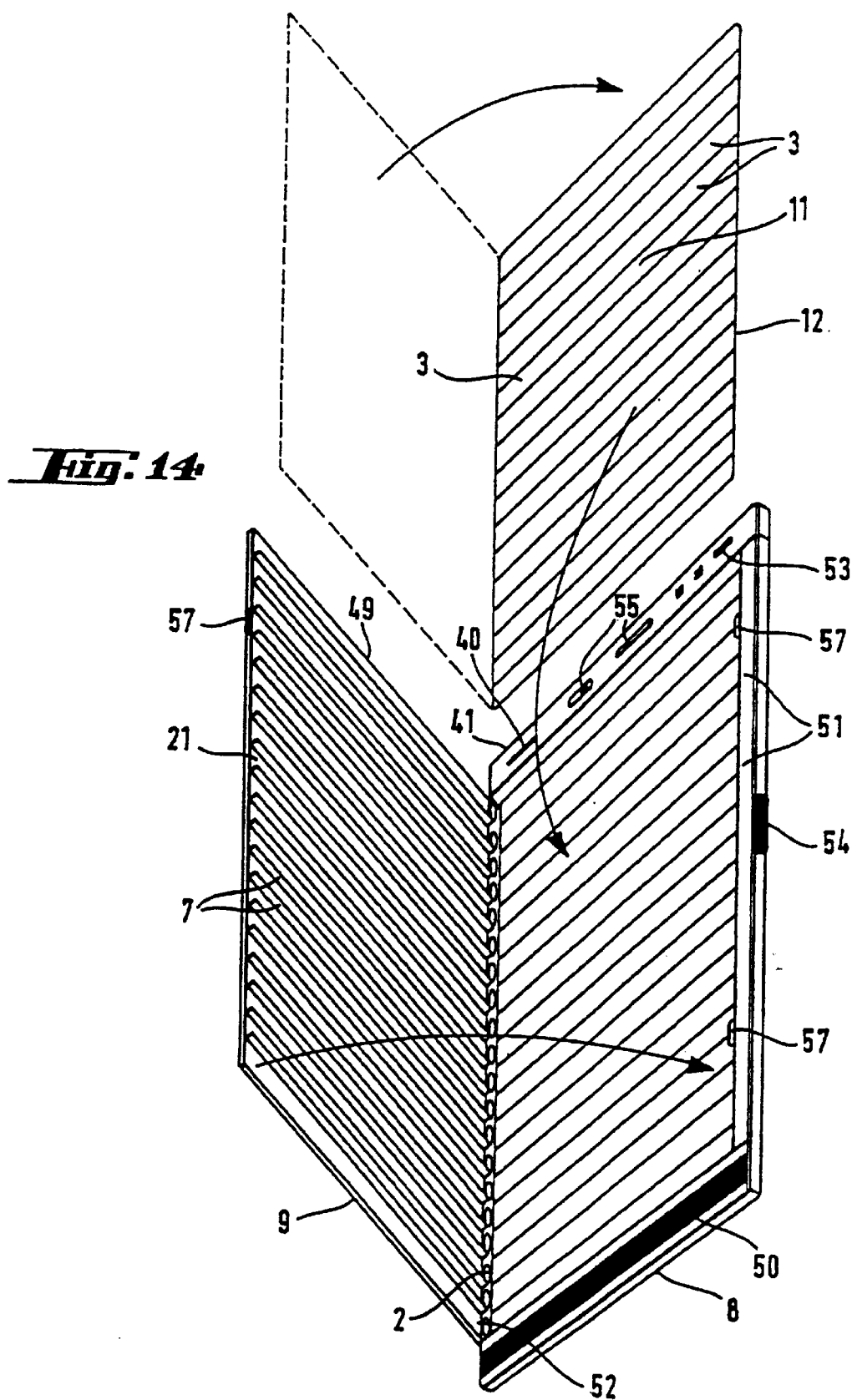

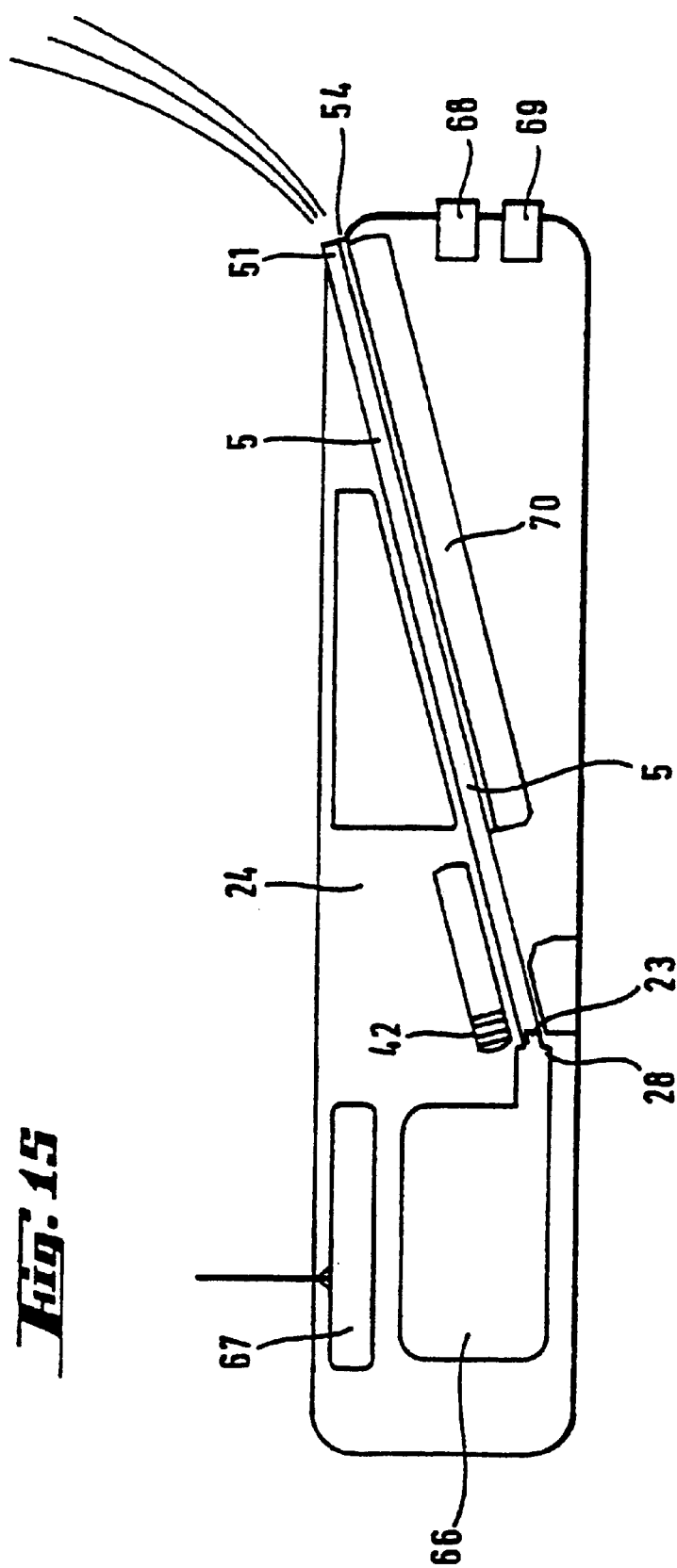

METHOD OF SUPPLYING SUBSTANCES TO BE DISPENSED INTO AIR

RELATED APPLICATION

This is a divisional application of U.S. Ser. No. 09/983,022, filed Jun. 8, 1998, and issued as U.S. Pat. No. 6,234,455, the latter being a continuation-in-part of U.S. Ser. No. 08/931,456, filed Sep. 17, 1997 and issued Nov. 3, 1998 as U.S. Pat. No. 5,832,320, the latter being a continuation of U.S. Ser. No. 08/781,028, filed Jan. 9, 1997 (now abandoned), the latter being a continuation of U.S. Ser. No. 08/232,050, filed Jun. 30, 1994 (now abandoned) and the latter corresponding is a continuation to International Application PCT/EP96/02925 filed on Mar. 7, 1996.

BACKGROUND AND OBJECTS OF THE INVENTION

The present invention relates to a device and a method of supplying substances to be dispensed into air or air mixtures. These substances to be dispensed are different scents in particular. Such presentation of scents would preferably be done for visual and/or acoustic stimuli and other events. In addition to scents, with another presentation, this could also be micro quantities of other substances which must be in aerosol form. The substances may also be in gaseous form. When "air" is mentioned below, it may also refer to air mixtures.

The invention thus also relates in particular to a method and a device for increasing the sensorial perception of visual and/or acoustic presentations, especially for decentralized media, e.g., in presenting television movies, video movies, radio broadcasts or musical performances, etc., wherein suitable scents are supplied to the viewers or listeners in synchronization with the presentation of certain visual and/or acoustic events (e.g., motion picture scenes).

Such a method and the respective equipment are described in the present applicant's patent application PCT/EP92/02446, here in particular in the description of FIGS. 16 and 17.

U.S. Pat. No. 5,273,690 discloses an air freshener device which can be used together with an air conditioning system, for example, to improve the air in rooms. This air freshener device has a carrier with multiple scents which are arranged in separate cells or compartments in rows or columns. The carrier comprises walls that can be ruptured for each cell or each compartment and are designed so that scents released can be dispensed in an oncoming stream of air. The carrier can be attached to a supporting structure with fastening elements so that the scents released can be distributed in an entire room by means of a stream of air.

According to this invention, a device for supplying substances to be dispensed into air, especially scents with a flat disk-shaped or plate-shaped base body having multiple separate channels running essentially parallel to its top and/or bottom sides to accommodate substances to be dispensed into air, with each channel having one inlet port and one outlet port, and wherein a stream of gas supplied to the inlet port can flow through the channels, wherein the inlet and outlet ports of at least one channel are sealed gastight until the substance is released and/or the substance is accommodated in a gastight manner in a reservoir in at least one channel that does not release the substance until the time for release of it.

In addition, the invention relates to a device for supplying substances to be dispensed in air, especially scents characterized by at least one hollow body provided with at least one air exchange port, where a stream of gas can flow through the interior;

at least one reservoir which is arranged in the hollow body for the substance to be released to the ambient air and is enclosed by a carrier material so that the substance can be released by destruction of the carrier material.

Destruction of the carrier material is understood to refer to the fact that the integrity of the carrier material is altered so that the substances to be dispensed are exposed. This can be accomplished by tearing off a part of a laminate, breaking a device and other methods of division.

According to another feature, the present invention relates to a reservoir with scent capsules that is self-activated by automatic detachment of a separation film on influx of air.

Another feature of the invention relates to a micro scent reservoir that can be played in decentralized scent dispensers, with the micro scent reservoirs optionally being designed in the form of a disk.

The device according to this invention for supplying substances to be dispensed into air has the advantages of being very small, handy and easy to package and ship. Additional advantages include the fact that the device can accommodate multiple substances that do not evaporate and cannot become mixed. The substances released can also be activated easily and can be protected well in transport.

The present invention, among other things, provides methods and a device where the various scent supplies (scent sets) belonging to an individual motion picture are fabricated and stored in a manner which ensures both storage of these scents (preferably 20–50 different scents per motion picture) in an extremely small space (compact disk) as well as perfect preservation and rapid, trouble-free shippability at low manufacturing costs.

Another feature of the invention is that a hard material reservoir consisting of easily separated halves is provided for substances that can be dispensed into air, especially scents.

According to another feature of the invention, a flat hard material protection is claimed, that protects stored substances such as scents that are to be dispensed into air from external environmental influences, such as pressure, impact, heat and damage:

Another feature concerns a flat scent reservoir with sealed scents that can be played, where the seals are not removed until immediately before playing.

In general terms, the invention presents a flat preservation system for multiple scent sets, especially a flat or disk-shaped hard material to protect pressure-sensitive and/or light- or heat-sensitive scent sets.

Another feature is a flat, hard material transport reservoir with protective tubes arranged in it to protect pressure-sensitive aromas.

Another feature of the present invention relates to a disk-shaped scent reservoir that is suitable for transport of encapsulated scents in a manner that protects them from pressure, temperature, moisture and light.

Furthermore, a method of releasing substances, especially aromas, to be dispensed into air, where the substances are microencapsulated and embedded in a carrier material which is characterized in that the scent microcapsules embedded in the carrier material can be broken open by the kinetic energy of a gas.

The invention thus creates a micro scent reservoirs system (scent disks) for automatic playing of event-based scent sets in decentralized scent dispensers (scent players), thus permitting a decentralized and yet synchronized scent accompaniment with motion pictures, music and other events.

According to a preferred embodiment of the method according to this invention for minimized storage and decentralized synchronized presentation of scents with visual and/or acoustic stimuli, the micro scent reservoirs equipped with the required aromas are manufactured in the form of very flat compact disks 1, such as those known for music CDs, for example.

This very small and flat embodiment of the scent carrier has the fundamental advantage that despite the relatively large scent contact areas, it nevertheless takes up very little space and thus permits mass distribution of the scent sets belonging to a certain motion picture to a large public.

Thus it is possible with scent set carriers of this form and type to glue them as inserts into a daily newspaper or television schedule or a product such as a package of coffee, etc. In this way, all the scents (scent sets) belonging with a television movie can be available to all interested viewers at the time of the broadcast without each individual television viewer having to purchase a scent CD for a motion picture he would like to see in the scented version.

By means of rapid, decentralized distribution of scent sets formulated precisely for a given motion picture and perfectly protected, and then added as an insert to a daily newspaper or television schedule or a postal mailing in the form of a flat scent compact disk, it is feasible for the scents (scent sets) belonging to a television movie or other media event to be in a perfectly preserved form at the time when they are dispersed to all interested viewers, without each individual television viewer having to go into a shop to purchase a new appropriate scent set for a motion picture that viewer would like to see in the scented version.

This permits for the first time rapid distribution, long-term storage and finally decentralized, synchronized playing of many different scent sets that fit precisely with a motion picture for a mass public to be distributed in a decentralized manner.

Here for the first time, a technique by which the carrier substance (e.g., air) automatically opens the sealed and preserved aroma out of the sealed state, gradually dissolves it and entrains it.

Thus with this technique, the aromas remain hermetically sealed off from air until the immediate time of presentation, so that premature aging processes are reliably prevented despite the fact that the substances are accommodated in an extremely small space.

Another application of these disks could also be in medical technology for administration of very small controlled doses of medication.

In contrast with computer diskettes and music CDs, which are flat binary information carriers, storage and distribution of scents is linked to the physical form of the scents.

The different supplies of micro scents are preferably applied to the inside of one of the two halves of such a disk in the form of a certain type of scent tracks (scent track arrangement).

Such scent track arrangements may also be stored in multiple layers one above the other in such a disk, because the individual layers are extremely thin and thus take up very little space. The individual tracks of such a scent track arrangement are partitioned off from one another by certain patterns of separating cuts. These separating cuts can be pressed as patterns into the respective half of the disk, or finally, they may be in the form indentations and elevations on the counterpart of the other half of the disk, where the individual tracks giving off the scent are ultimately formed by the manufacturing process, while the disk halves are joined in a certain manner.

To prevent mixing of the individual scents and aromas from the scent tracks during storage of the disk, these tracks are preferably designed in such a way that small, individually separated protective channels are formed in production of the disk and demarcate the individual scent tracks from one another.

Within the separate scent channels, the scents are preferably sealed once again in scent carrying slotted channels to protect them from the action of oxidation processes in addition to outside scents.

A third sealing of the scents can also be achieved by encapsulation, by sealing the scents another time in very small microcapsules inside the scent carrying slotted channels, so that the microcapsules rupture simultaneously with the opening of the slotted channels.

The diameter of the separating channels and the elevation due to the second sealing of the scents are preferably designed so that the total thickness of the scent CD is only on the order of that of commercial music CDs and CD ROMs, or at least it is so slightly greater that these scent CDs can still be glued to a newspaper as an insert with no problem.

If a motion picture is to be played back over TV or a video player, the signals assigned to a scent can be played through the respective television transmitter or over the storage medium together with the video and audio signals of the motion picture, as already described in the present patent applicant's patent PCT/EP92/02446 (FIGS. 16 and 17).

These signals act directly or indirectly on a playback apparatus, the so-called scent player, into which the scent disks described above are placed before starting the motion picture.

If one of these scent tracks is activated by a scent signal, a carrier medium, which may be air or a certain air mixture, is driven by a small pump and pumped into the respective scent channel on the scent disk through a micro filling connection. Certain very thin scent carrying layers are then activated within the scent channel by the pressure provided by the carrier medium.

The signals for triggering the scents may also influence additional features of a scented motion picture presentation, such as the quantity of air flowing through a scent carrier, the temperature of the scent-air mixture dispensed, the length of the scent interval, optionally any intended mixing of scents due to their simultaneous activation or overlaying one scent over another.

If, in a modification of the intended equipment, the intent is to also present theater, music or motion picture presentations accompanied by scents in public theaters, etc., the invention also makes it easy to minimize the cost of renovating such buildings (as described in PCT/EP92/02446) by omitting the scent line installations normally required for this purpose. Instead of the central scent playing device and the complete line system, a small playback apparatus is mounted at any desired location. This is important in particular when there are plans to accompany only certain presentations with scents over a limited period of time, when then would not justify the cost of a complete renovation of the theater under some circumstances. This device can also permit scents to accompany open air presentations.

With the creation of a novel multiple-scent reservoir system that can be played back automatically and can easily be distributed through mass media such as newspapers due to extensive miniaturization, the invention also makes it possible to use this system for any desired decentralized application.

In addition to using this system for motion pictures, it is thus also possible to use this system for other media, such as advertising, or for automatic food and beverage dispensers, computer games or on-line purchasing accompanied by scents, music CDs, product information units (e.g., information computer at the point of sale) and any type of presentation that can be enhanced by the addition of scents either centrally or from decentralized sites.

Like the other decentralized applications already mentioned, the recently available data helmets, VR helmets and equipment for experiencing virtual reality, cyberspace adventures, etc. also offer a possibility for using these rapidly dispersable and optimally preserved micro scents.

DESCRIPTION OF THE DRAWINGS

This invention is further explained below with reference to the figures which show the following:

FIG. 3: a cross section through various variations of the scent CD from FIG. 1;

FIG. 4a: a half cross section through the scent compact disk/scent CD from FIG. 1 in the unactivated state;

FIG. 4b: a half cross section through the scent compact disk/scent CD from FIG. 1 in the partially activated state;

FIG. 4c: a partial cross section through the scent compact disk/scent CD from FIG. 1 in the fully activated state;

FIG. 5: an exploded diagram of the scent CD from FIG. 1 with different function layers;

FIG. 6: another embodiment of a scent compact disk with playback demarcation and nation-specific filter codes, and a partial diagram of a playback device;

FIG. 7: another embodiment of the scent CD;

FIG. 7a: a variation of the embodiment according to FIG. 7;

FIG. 8: a partial cross section through another embodiment of a scent compact disk;

FIG. 9: a lower disk frame of another embodiment of the scent CD;

FIG. 14: another one-piece embodiment of the scent CD as a folding disk;

FIG. 15: a schematic cross section through a playback apparatus 24.

DESCRIPTION OF PREFERRED EMBODIMENTS OF THE INVENTION

Figure 1:
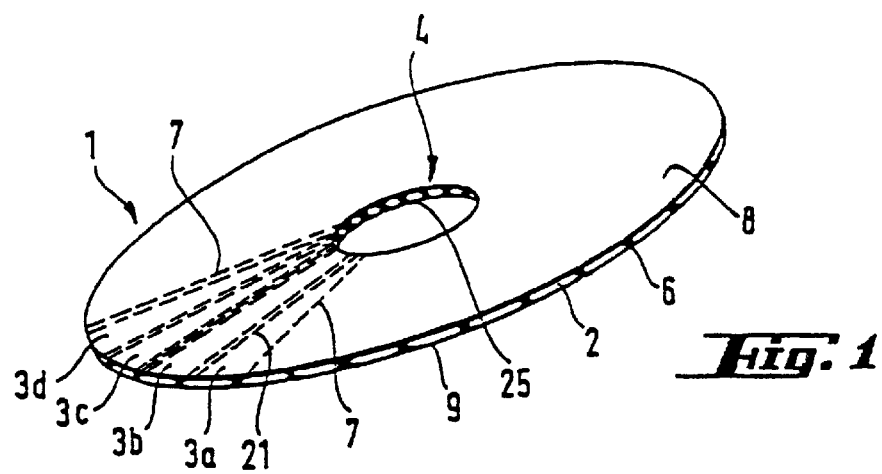
FIG. 1: a scent compact disk or a scent CD.

The embodiment of this invention illustrated in FIG. 1 and in FIGS. 2a through 5 shows a flat scent compact disk/scent CD (1) in which a large number (i.e., preferably between 5 and 50) different scents are stored in an extremely small space within a very small flat disk where they are also preserved perfectly.

Such scent CDs serve fundamentally to permit playback in small playback apparatuses (FIG. 15) independently of large machines, as already described in FIGS. 16 and 17 of PCT/EP92/02446 (for a scent medium to be played back vertically by the scent carrier, although this is not yet practically feasible). The extremely flat scent CDs which are proposed in the present invention and can be played in small decentralized playback apparatuses make it possible here for the first time to play back event-based (e.g., motion picture) sets of many different scents in a synchronized manner at any desired location, in perfect quality and at the same time individually adapted to the personal perception of the consumer or observer.

These multiple scent sets, each precisely adapted to a certain event or motion picture, which can also be preserved for long periods of time, also permit for the first time a very rapid and inexpensive distribution, e.g., by mail, to a mass public with a decentralized distribution due to their small and preferably flat construction.

Figure 2A:
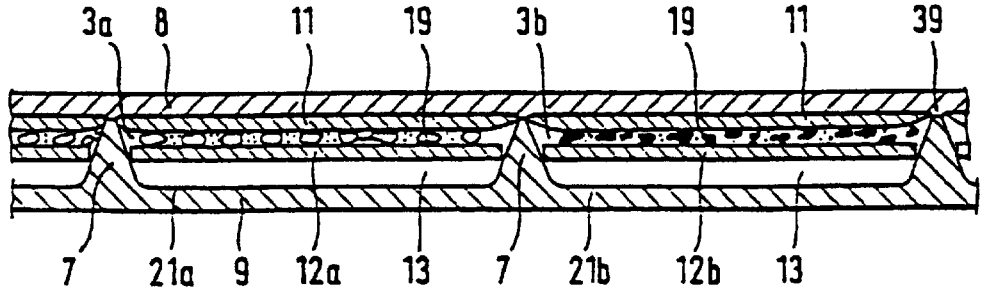
FIG. 2a: a partial section through the scent compact disk/scent CD from FIG. 1 with slotted channels in the unactivated state.

With such a scent compact disk/scent CD (1), each individual scent of the various scents is first stored in a separate, extremely flat slotted channel 3a, 3b, 3c, etc. (FIGS. 1, 2a and 4a), where each of these slotted channels is in turn accommodated in another very flat protective tube 21a, 21b, etc., which hermetically seal the different scents with respect to each other in the slotted channels 3a, 3b, 3c, etc. (FIG. 2a). In the present embodiment, these tubes are accommodated radially on the scent CD 1 (FIG. 1).

The numerous protective tubes 21a, 21b, etc. which are arranged around the scent carrying slotted channels 3a, b, c, etc. are formed by an upper disk half 8, a lower disk half 9 and lateral channel separations 6 in the form of elongated dividing webs 7 on both sides in the scent compact disk 1 (FIGS. 1 and 2a).

The protective tubes 21 thus form small, flat, radially arranged tunnels in which the slotted channels 2 running across the scent CD are also protected from external environmental influences such as heat, pressure and damage (FIG. 2a). This protective function becomes especially important due to the fact that the slotted channels 3 are preferably designed so they are sensitive to pressure (FIGS. 2a and 4a), which is explained in greater detail below.

To optimally utilize the small amount of space available on the scent CD, the slotted channels 3 in the present embodiment preferably run in a conical form from the edge of the disk, where the inlet 2 of each slotted channel 3 is located, to an outlet panel 4 toward the inside.

The inlet 2 and outlet 25 of the slotted channels 3 may be provided with seals 10 and 22 (FIG. 4a) to additionally preserve the scents, with these seals being opened as soon as the disk is placed in a playback apparatus or not until it is actually played back by the playback apparatus (FIG. 4b).

In the preferred manner of storage of the scents within the slotted channels 3, these seals may be eliminated under some circumstances because long-lasting preservation is ensured by the present embodiment of the disk, as explained in greater detail below.

The scents are preferably applied to the insides of slotted channels 3 in the form of microscopically small, so-called micro scent capsules 19 (FIGS. 2a and 4a), with the scents being completely enclosed by the microencapsulation, which guarantees very good preservation in an extremely small space due to the exclusion of oxygen. (Microencapsulation of extremely small quantities of substances in liquid form and in other forms is a method that has long been known in the printing industry.)

In addition, there is additional preservation of the scents due to the fact that the slotted channels 3 wherein the encapsulated scents are stored are enclosed yet again by a protective and sealing tube, protective sheathing 21.

Protective sheathing 21 also has the function of protecting the micro scent capsules 19 in the slotted channels 3 from the effects of mechanical pressure and other pressure as well as light, heat, moisture and other influences, because the micro scent capsules can be opened prematurely relatively easily if a slotted channel 3 is compressed, for example.

This also plays an important role in transport of these scent disks with the various resulting mechanical stresses, etc., because if the micro scent capsules 19 were opened prematurely, the scent would also begin to be released, age and oxidize prematurely, which could result in a considerable impairment of the scent impression.

Each individual scent is thus sealed and preserved in three ways in the present embodiment:
1) in the protective sheathing 21 (protection from mechanical pressure, oxygen and mixing),
2) in the slotted channels 3 (protection from mixing and oxidation),
3) in the micro scent capsules 19 (protection from oxidation),
thus making it possible to achieve a very reliable preservation and storage of many different scents (e.g., 40) in an extremely small space (scent CD).

For scene-specific scent accompaniment of a TV motion picture or other event, the scent CD is placed in an appropriate playback apparatus, wherein the functioning of such a playback apparatus is already substantially described in patent application PCT/EP92/02446 by the present applicant. The flow paths here are many times longer due to the fact that, in contrast with said previous patent application, the transport medium, e.g., air in the present embodiment, does not flow by the shortest path—namely across the scent carrier—but instead it flows longitudinally through the slotted channels 3 arranged in the disk in a flat manner. Thus, the surface of the individual scents is enlarged significantly while the space required by the playback medium is very small, thus permitting a more accurate presentation of scents as well as permitting playback in various intensities.

On the other hand, with the longer flow paths in the extremely flat construction of the scent CD, the pressure required for playback is much higher, which is why no tangential blower is provided as the pump drive of such a playback apparatus for scent compact disks, as described in the previous application, but instead one of the known types of pumps for air and gaseous media such as a normal aquarium pump or diaphragm pump 66 is used (FIG. 15). Apart from further suitable pump types such as compressor pumps, also very small, compressor-like or turbine-like pumps can be used for this purpose.

In a presentation of these scents to accompany a motion picture or music, a technique is implemented for the first time whereby the carrier substance (e.g., air) automatically opens the sealed and preserved scent out of the sealed state, gradually releasing it from the hermetic seal in which it is preserved, and then entraining the scent and transporting it to the consumer.

The carrier medium here opens the scent bottle itself, so to speak, and then automatically becomes enriched with the scents belonging to a certain scene in the motion picture.

With this technique, the scents remain sealed off from air until the immediate time of presentation, so that despite the fact that they are accommodated in an extremely small space, premature aging processes are reliably prevented.

For scene-specific development and release of scents desired for a motion picture, first a scent CD 1 produced to fit precisely with the events in that motion picture is placed in a suitable playback apparatus.

Within the playback apparatus 24, a small inlet nozzle 23 is automatically inserted into the slotted channel inlet 2 of the scent to be played back first, while another outlet nozzle 27 is inserted into the outlet 25 of the slotted channel 3 which is placed on the inside of scent CD 1 (FIG. 4b).

As soon as the corresponding scent which is desired for a certain scene is to be played back while a motion picture is running, a corresponding signal which can be identified by the playback apparatus, e.g., by a suitable signal receiver 67 (FIG. 15), is played or transmitted together with the motion picture.

In this way, the proposed gaseous transport medium, preferably air, is activated within the playback apparatus 24 by means of a pump (not shown) and pumped through inlet nozzle 23 into the inlet 2 of the slotted channel 3a belonging to the first desired scene scent A.

Due to the pressure which then builds up, first the walls at inlet 2 of slotted channel 3a, preferably made of a scent carrying film top side 11 and a scent carrying separating film 12a (FIG. 5) for the purpose of simple fabrication, are pressed apart radially to the axis of flow (FIG. 4b).

In order for the air stream to continue to the end of the slotted channel 3 and not be able to escape at the sides, preferably certain parts of the film sides 11 and 12 of the slotted channel 3 are connected to each other and also in part to the disk halves 8 and 9.

Thus, films 11 and 12 can each be connected on both sides to a lateral film joint 30 next to each slotted channel 3, so they are separated shortly after the scent carrying parts of the films.

In a modified form of slotted channel 3k (FIG. 3), these lateral joints 30 also remain between films 11 and 12, and on activation of this modified slotted channel 3k, there preferably results a small, flat, scent carrying channel 33 which persists as a scent channel during playback operation, without connections 30 being released (see the three right channels in FIG. 3).

Such a lateral connection 30 next to slotted channels 3 may come about as a glued joint, a hot glue joint, a grooved seam, a folded seam or a punched joint, or due to the fact that the dividing webs 7 of the bottom half 9 of the disk come in contact with the top half 8 of the disk in such a way that in this way the lateral connections 30 between films 11 and 12 are created (as in FIG. 3, for example).

Likewise, on the top half 8 of the disk there may be upper dividing webs 46 which work together with the bottom half 9 of the disk or its dividing webs 7 to establish the separations for the individual scent channels.

In a slight modification of the slotted channel 3k shown in FIG. 3 (second protective tube 21 from the left), it may also be provided with an additional material, optionally slightly folded (FIG. 8), so that slotted channel 3k is completely in contact with the walls of the protective channel 21 when air flows through, thus yielding a greater flow-through volume (FIG. 8) than in the design of a flat channel 33 (as in the two right protective tubes 21 in FIG. 3).

In another modification of the slotted channel 3k shown in FIG. 3, it is made of one piece instead of two films 11 and 12, with the scents applied to the walls of this one-piece flat channel during the manufacturing process. Thereafter, however, the channel can likewise be folded flat, pressed or bent and then accommodated in a protective tube 21.

Such flat channels can also be provided with seals 10 and 22 at the ends or with closing perforations, gluings, folds, etc., which are opened when the carrier material first flows through them.

It is also possible here to set up such flat channels during the manufacturing process in such a way that the walls of these channels are under an internal tension, either partially or completely or only at the ends. If air flows into such channels and builds up a certain pressure there, then the areas of these channels that are under a slight pressure will rupture, thus completely allowing air and scents, etc. to flow through.

To stabilize the air stream, preferably the scent carrying top side 11 of the film is joined to the top half 8 of the disk in FIGS. 4*a–c*, and at least the front end of the bottom separating films 12 is joined to a connection 45 and the rear end is linked by another connection 47 to the bottom half 9 of the disk (FIG. 4*b*).

The pressure that then builds up further at slotted channel inlet 2 (FIG. 4*b*) is propagated finally toward the interior of the slotted channel 3*a* (FIG. 4*c*), with the top side 11 of the film and the scent carrying separating film 12*a* being separated from each other along their length as far as outlet 25, and with the separating film 12*a* being pressed into the displacement cavity 13 (FIGS. 4*a–c* and 2*b*).

Inasmuch as the top side 11 of the film and the separating film 12 are each connected to a connection 30 at the edge of a slotted channel 3*k* (as in FIG. 3), the separating film 12 becomes detached from the top side of the film only in the middle area, then forming flat channel 33 (the three right channels in FIG. 3).

Figure 2B:
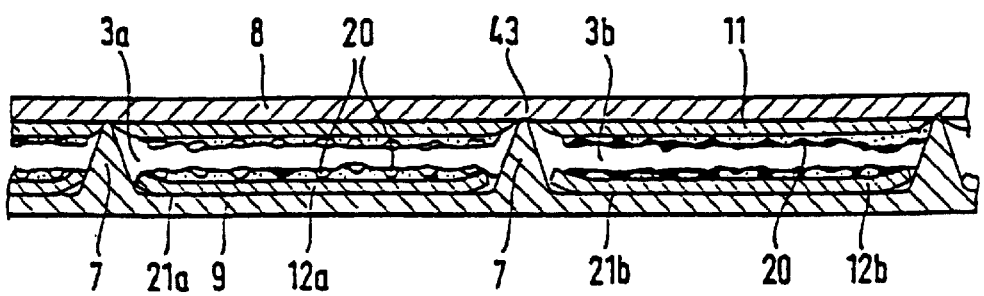
FIG. 2b: a partial section through the scent compact disk/scent CD from FIG. 1 with slotted channels in the activated state.

Then the micro scent capsules 19 that are connected to films 11 and 12 are torn apart and opened, thus releasing the scents that had been sealed until then, so they are then entrained by the additional air forced in (FIGS. 4*c* and 2*b*). If the films 11 and 12 of a slotted channel 3 have become detached from one another and the scents previously sealed in the micro scent capsules have been released from their preserved form, the air stream 29 which is then enriched with scents is next sent through protective tubes 21*a–x* and conveyed further through outlet 14 to the outlet nozzle 27 (FIG. 4*c*).

The air 29, which is then enriched with the scents belonging with a certain scene, is conveyed further out of the playback apparatus and to the viewer after leaving the slotted channel 3*a* of scent CD 1, so that, for example, in a scene of a motion picture where an orange is scene, the scent of an orange can also be perceived (FIG. 15).

Playback of the next scent belonging with another scene then takes place by triggering and moving the scent CD 1 inside the playback apparatus 24 by means of additional appropriate signals in such a way that the proper scent can also be played, with the two inlet and outlet nozzles 23 and 27 being lifted briefly away from the scent CD and then inserted into the slotted channel 3*b* and the protective tube 21*b* of the next scent.

In a variation of the present embodiment, the flow of air inside the scent CD can also take place in the opposite direction, from the inside to the outside instead of from the outside to the inside, with the inlet nozzle 23 being reversed to function as the outlet nozzle 27 and vice versa. The enriched air is then also directed from the respective other scent outlet to the viewer accordingly.

To be able to actually accommodate all 30, 50 or more scents required for a motion picture, a piece of music, etc., on a single scent CD, it is also advantageous to keep the respective area needed for a scent as small as possible through certain design measures.

The area needed to be able to accommodate an encapsulated scent on a scent CD on the whole can first of all be influenced by how tightly the scent capsules are applied in the scent carrying layers of the scent CD and how large the individual capsules are.

In addition, the intensity of the scent mixture which is selected as the basis of the encapsulation process may also influence the required scent area.

Therefore, in order to be able to accommodate as many scents as possible on a scent CD with the present scent CDs, especially intense mixtures of the scents to be encapsulated and at the same time as many scent capsules as possible are preferably applied per unit of area so that only a small amount of area is required per scent.

To maintain maximum scene accuracy and avoid any superimposing of scents, the measures proposed for central playback equipment in a previous patent application PCT/EP92/02446 (FIGS. 16 and 17) (measures which function here for the first time in contrast with all previous proposals), i.e., extreme minimization of the amount of air used, specification of the scent path and minimization of the lines used, can also be used in the present playback apparatus.

The scent quantities retrieved from the scent CD by the playback apparatus are therefore on an extremely low level, i.e., amounting preferably to one thousandth to one ten thousandth of the volume capacity of an air conditioning system and are also conveyed in a relatively bundled form to the viewer, as also proposed in PCT/EP92/02446. The scents can therefore be perceived only in a very small area around the nose of the viewer, which makes it possible to work with especially small quantities of scent.

In addition to the measures proposed previously, this also makes it possible to accommodate the scents in a very small space inside the scent CD.

In one embodiment of the playback apparatus with decentralized control (not shown here) preferably only between 0.0001 and 0.5 liter of scented air per second is used. In another preferred embodiment of the decentralized playback apparatus, between 0.003 and 0.3 liter per second is used, and in an especially preferred embodiment of the invention, between 0.01 and 0.2 liter per second is used.

This also makes it possible to design very accurately the course of a scent presentation, because such small quantities of scent are volatilized very rapidly, thus permitting an accurate scene-specific presentation.

Due to the scent impressions that can be perceived essentially only in the area of an individual viewer's nose, it is likewise possible to make these small quantities of scent adjustable individually for this viewer or for each viewer otherwise.

This adjustability of the quantities of scent dispensed is important in particular due to the fact that the sensitivity of consumers' noses to odors often varies greatly.

With a preferred playback apparatus, the intensity of the scent presentations can be adjusted accordingly, so that each consumer can enjoy the intensity of the presentation he would prefer. In addition, with more expensive embodiments of the playback apparatus, it would also be possible to influence individually the temperature, quantity and scent cycle duration of the scents presented.

If a consumer enjoys motion picture presentations accompanied by scents but has a specific aversion to certain scents, it is also possible with the present playback apparatus to classify these scents in classes, with the user being able to more or less "vote against" any scent classes he does not want. The control signals for these unwanted scents are then simply ignored by the playback apparatus and these scents are then skipped.

The corresponding individual set-up of a scent presentation is explained further below in the description of FIG. 6.

For the purpose of easy manufacturing, scent CD 1 is preferably composed of four function layers during the manufacturing process, namely of the top half 8 of the disk, the scent carrying film top side 11, the scent carrying separating film 12 and the bottom half 9 of the disk which is usually provided with dividing webs 7 (FIG. 5). During manufacture, the individual function layers 8, 9, 11 and 12 are then pressed together and welded in part (e.g., by ultrasonic welding), resulting in the individual function features of the scent CD, as provided and described above, due to the shape and properties of the individual layers (FIGS. 1 and 5). Slotted channels 3 are preferably formed by pressing and, in part, gluing layers 11 and 12 together, with the segmentation of slotted channels 3*a*, 3*b*, etc., and of separating films 12*a*, 12*b*, etc., formed by the contact of dividing webs 7, which are preferably provided on the bottom half 9 of the disk, with the top half 8 of the disk.

In order to achieve a tight connection between the bottom half 9 of the disk or the dividing webs 7 on it and the top half 8 of the disk to produce small, air-pressure-resistant protective tubes 21*a–x*, the tips of the dividing webs 7 can be joined to the top half 8 of the disk by various methods (for example, with ultrasonic welded joints 39, as shown in FIG. 2*a*, or with plug or glued connections).

In this way, the different scent tracks of films 11 and 12 (FIG. 5) applied to at least one of the films by a type of printing method can also be segmented. Such a segmentation, preferably air-pressure-resistant, is advantageous to this extent because this prevents the air stream from flowing into an adjacent channel during activation of one slotted channel 3, which could thus result in an unwanted mixed scent.

The joints of the dividing webs 7 and the other half of the disk can also be formed through the scent carrying films 11 and 12, e.g., as plug connections or glued joints.

With a plug connection, the films are pinched at the edge, whereas the films, which are made of plastic in an ultrasonic welded joint 39, for example, are heated briefly in the area of the contacting dividing webs 7 and are welded together in the process. A glued joint with films made of cellulose, for example, can be formed, e.g., by the adhesive penetrating through capillaries or through small perforation holes through the films to the other half of the disk, thus segmenting the scent tracks.

In another modification of the process of manufacturing the scent CDs, scent carrying separating films 12*a–x* are initially also left as a cohesive film 12 after applying the scents (FIG. 5), where the individual scents here are also applied or printed onto the total film 12 without dividing it into individual separating films 12*a*, 12*b*, etc.

Individual scent lamellas are then preferably predesignated by means of small cuts in the film surface (a type of predetermined breaking points). In addition, scent carrying top side 11 of the film is omitted here, and the separating film 12 together with the various micro scent capsules 19 of the individual scent tracks is glued to the top half 8 of the disk.

When the bottom half 9 and top half 8 of the disk to which the presegmented separating film 12 with all the required scents has already been glued are joined or pressed together, the dividing webs 7 of the bottom half of the disk thus come in contact with the top half, so that the scent carrying separating films 12 are divided into individual films 12*a*, 12*b*, etc. Finally, the scent carrying slotted channels 3*a–3x* are formed between the separating films 12 and the top half 8 of the disk and are hermetically sealed from each other by the dividing webs 7.

In additional embodiments (not shown) of the invention, various combinations of the components of individual embodiments of the scent CDs plus variations and modifications of the manufacturing processes described here for production of similarly functioning scent disks are also conceivable.

The scents which are ultimately presented by the present playback apparatus can also be modified in their form of presentation to perfect the scent impression.

An important improvement in the scent impression can be achieved in certain cases, e.g., if they are also warmed or heated by a small heating element (not shown) before or at the time of dispensation to the viewer, in order to present the typical scent impression of hot coffee, for example, even more accurately.

Such heating can preferably also be achieved by the fact that the scents to be heated are diverted by a deflecting valve into another channel leading to a suitable, preheated micro heating element before reaching the viewer. Such a method is advantageous in particular when the heating elements used in the playback apparatus are too slow to be heated very rapidly in a film showing and then be cooled again briefly with the next scent.

Conversely, with the present playback apparatus (not shown), it may also be possible to cool the scents flowing toward the viewer in order to thereby imitate the scent impression, e.g., of ice cream or a cool autumn breeze.

In a somewhat more complicated playback apparatus (not shown), a further improvement in the scents retrieved from the disk by the playback apparatus can also be achieved in certain aromas and scents if they are enriched with some moisture before being dispensed to the viewer.

Thus, for example, the scent impression of a rain-moistened meadow can be perfected if the meadow scent, which is stored in a relatively dry condition and is retrieved by normal air, is subsequently passed through a moisturizer (not shown).

Accordingly, the retrieved medium itself, such as air, can also be enriched with moisture before passing through the disk.

Such a moisturizer may also be provided on the disk itself, so that the carrier medium can be passed through a suitable moisture micro chamber (not shown), e.g., through a type of permeable moisturizing pad, before or after penetrating into the diffusing channels.

Such moisturizing of the scented air may also be achieved on the disk by means of microencapsulated moisture which is then released by a method similar to that used with the release of scents from microcapsules described above.

If a sharp, vertical alignment of the exiting air enriched with scents is desired with the present playback apparatus, the carrier medium, such as air, with a decentralized playback apparatus can also be mixed with certain quantities of helium (which is absolutely harmless for humans, because divers and even asthmatics can breathe better in this way) The helium can be accommodated in small cartridges resembling $CO_2$ cartridges in syphon bottles inside the playback apparatus (not shown).

For example, it is also possible for the scents to be first retrieved by a microcurrent of helium from the cartridge. As described above, the area or space in which the scents are accommodated in the disk is preferably minimized by various measures, e.g., intensification of the scent output base, so it is possible to use only very small quantities of helium for the actual retrieval of the scent.

This mixture of extremely small quantities of helium and intense scent is then mixed with a somewhat larger stream of air to dilute it to the normal scent intensity and then finally it is transported to the viewer.

This diluted stream of air can also be provided with moisture in advance, as described above, or it may also be heated. Cartridges that are used only for retrieving scents can also be filled with substances other than helium.

In another embodiment of the scent compact disk 1, which is shown in the first channel on the left in FIG. 3, no micro scent capsules 19 are accommodated in the slotted channels 3, but instead other scent carrying materials 26, which are also arranged in an extremely flat manner, are accommodated there, where in this case films 11 and 12 do not completely move apart with an influx of air mass under pressure, but instead they remain as a sleeve or modified flat channel 44 around the respective material 26. The air then flows through the permeable or semipermeable scent carrying material 26.

The protective tubes 21a, 21b, etc. which are around the modified flat channels 44 and hermetically seal them from each other (FIG. 2a) are, however, preferably provided with seals 10 and 22 at inlet 2 and outlet 25 in this case, because the possibilities for preservation of these other materials 26 would not extend as far as with micro scent capsules. In this case, very thin and flat nonwovens can also be used as the scent carrying materials 26.

These nonwovens are preferably attached to the edge of the modified flat channels 44.

In a variation of this embodiment of a scent CD various forms of micro storage for scents can also be combined within one scent CD, as shown in FIG. 3. Thus, the scents here can be stored and preserved over scent carrying materials 26 in the left channel and over micro scent capsules 19 in other channels.

This embodiment is recommended in particular if one of the few scents with which microencapsulation is difficult to implement, such as the aroma of coffee, is to be used with the movie that is to be accompanied. Thus both encapsulated scents and other scents in different forms of storage can be stored in the optimum possible manner on such a scent CD.

Due to the great variability in composition of scents, very different encapsulation methods are partly also necessary for storage in some cases. Therefore, each scent is preferably produced and applied with the optimum encapsulation method for it for use in a scent CD.

If other methods that yield an optimum result for storage of specific scents are considered, they are used on other scent tracks accordingly, so that the optimum scent storage method is used on each scent track.

Thus, for example, sensitive scents can be stored in the form of a scent resin, scent gels or other combinations of scents and carrier materials. If the corresponding forms of storage are not combined with a method of encapsulation of the scents, for better conservation, these scent tracks are usually provided with seals 10 and 22 at the inlet and outlet, e.g., as illustrated in FIG. 4a.

To further reduce the differences in stability of scents which are encapsulated and also stored with other methods, other methods of preservation can also be used in addition to the seals 10 and 22.

The scent carrying tracks of the scents on the disk that have not been encapsulated are also filled with small quantities of substances that prevent premature aging and oxidation. Thus, for example, the modified flat channels 44 (FIG. 3) can be filled therewith or, if scent carrying nonwovens are used, for example, and are applied directly to the wall of a slotted channel 3 (for example, like the open tracks shown in FIGS. 2a or 4a), then the slotted channels 3 themselves may also be filled with them.

These are preferably gaseous substances which are retained within the respective scent track after filling by means of seals 10 and 22. Such oxidation inhibitors 62 may be, for example, very small quantities of helium or carbon dioxide which are placed in the corresponding scent tracks on the disk. Other gaseous substances such as those also used in preserving foods and beverages can also conceivably be used.

As another method, it is also possible to produce a more or less strong vacuum in the disk after filling with scents, before applying the seals 10 and 22. If the seals 10 and 22 are sealed, a vacuum remains in the sealed scent tracks, so that no oxygen or other substances that would accelerate the aging process can reach the sensitive scents which are not encapsulated.

As soon as seals 10 and 22 are opened in playback, the vacuum is finally eliminated, whereupon the presentation of the corresponding scent can begin. If small quantities of oxidation inhibitors are used instead, they are forced automatically out of the scent track by the scent carrying substances, such as air, in playing disk.

In another embodiment of such mixed disks (not shown here) which have scent tracks with encapsulated scents as well as scents that are not encapsulated, disks can be manufactured where all scent tracks are stored in the form of the types of unencapsulated storage described above. Although such disks, despite the various preservation methods described above, probably do not have the stability of disks in which all the scents are encapsulated, they can be used for short-term demand under some circumstances.

The additional preferred embodiment of a scent CD 5 shown in FIG. 6 completely avoids the sometimes complicated rotation of the S-CD for playback of each following scent and the associated lifting and re-engagement of the inlet and outlet nozzles 23 and 27 into the inlet 2 and outlet 25 of the corresponding new scent.

For this purpose, after insertion of the scent CD, which is rectangular here, for example, into the playback apparatus, an inlet nozzle panel 28 is inserted into the slotted channel inlets 2 of the scents, where there is a separate inlet nozzle 23 for each individual scent with its own control valve 48. Seals 10 optionally provided at the inlets 2 of the scent carrying slotted channels 3a, b, etc. are opened when the scent CD is connected to the playback apparatus 24 through the inlet nozzles 23. For the intended exchange of one scent with another, in this embodiment it is necessary only to switch to the new line to the other inlet nozzle 23.

Such a method of controlling the scent disk should greatly simplify the manufacture and functioning of the playback apparatus because there are almost no moving parts or susceptible mechanical parts (FIG. 15).

Here again, as described above, micro scent capsules 19 are preferably used, and they automatically rupture due to the separation of separating films 12, etc. when air 18 flows into the respective slotted channel 3 and thus are automatically released to the air stream. The air 29 enriched with scents is advanced further by the air coming after and flows to an aligning device 51 which collects the various air streams of the individual activated scent channels 21 and directs them to a focusing outlet nozzle 54. Finally, in the operating mode, the focusing outlet nozzle 54 has a connection to the playback apparatus, from which the activated scents are finally transported to the viewer and/or listener by means of another short piece of line (FIG. 6).

The aligning device 51 that collects the air streams and the focusing outlet nozzle 54 are preferably part of the scent disk 5 itself. If deposits of different scents develop in these scent lines with prolonged operation, which could result in unwanted superimposition of scents from previous presentations over a period of time, this has the advantage that these scent lines are replaced each time a scent CD is changed (FIG. 6).

In a preferred modification of the embodiment described here, the scent stream exiting from the focusing outlet nozzle 54 of the scent CD 5 is sent directly from the scent CD to the viewer without an additional piece of line in the playback apparatus (FIGS. 6 and 15).

Finally, it is thus possible for the scents presented by the playback apparatus not to come in contact with the playback apparatus in any way. This has the advantage that even with very extensive use of such a playback apparatus for scent CDs, deposits of scents cannot develop anywhere in the apparatus over a period of time. This can be a user-friendly simplification in the sense of maintenance-free handling (FIG. 15).

In this variant of the presentation arrangement, the scent CD is preferably not stored flat inside the playback apparatus but instead is arranged at an inclination, e.g., at an angle of 30°, so that the scents in the scent CD can also flow out to the viewer at a slightly inclined angle (FIG. 15).

If, in other embodiments of the playback apparatus 24 (not shown here), the scents nevertheless pass through a long piece of lines and possibly devices within the playback apparatus after leaving the scent CD 5, this could over a period of time result in rather unpleasant odors of scents deposited from previous presentations. In this case, a special cleaning disk (not shown) is prepared for such a playback apparatus, where a nonwoven or similar material with a cleaning fluid is provided in the protective tubes 21 instead of scent carrying slotted channels and can then flow through the corresponding contaminated lines of the playback apparatus in operation and then can finally be collected.

Then when a scent in the scent CD is played in a presentation (which is indicated schematically in FIG. 6), only the valve 48 of the corresponding slotted channel 3 is opened. The tendency toward a back-up to possibly develop through the aligning device 51 into other scent carrying protective channels 21 or slotted channels 3 is largely suppressed by the fact that the valves 48 for the other scents remain closed, and thus no reverse air flow with possible mixing of scents can take place.

Additional protection from such a back-up can be ensured by the fact that small outlet valves 56 that allow air flow essentially only in the direction of the aligning device 51 are provided at the end of the scent carrying protective tubes 21 just before the point of transfer into the air stream aligning device 51.

Since the scents already come in contact with oxygen and other materials after the first playback, they already begin to age after the first playback of the scents, which is still perfect.

To prevent scents from being played back in a very aged and possible less pleasant form (which would not give this new medium a good reputation) at a second playback of this scent disk, possibly at a much later time, the scent CDs of all the embodiments described here are preferably designed so that they can be played back only once or only to a limited extent.

This limited playback capability can be achieved with the embodiment illustrated in FIG. 6, for example, by providing inside the scent CD 5 a small marking tab 40 that is accessible from the outside only through a small sampling port 41 (FIG. 6).

If the playback apparatus is then instructed to start operation of the playback mode, first a pin 42 (FIG. 6) which is in the playback apparatus 24 an d fits exactly through the sampling port 41 is inserted into the scent CD 5. If the sampling pin 42 detects that the marking tab 40 is still present, the scent CD is then released for playback operation.

After the start of playback operation, the sampling pin 42 is finally inserted a certain distance further into the scent CD 5, whereupon the marking tab 40 is bent over or destroyed. This ultimately documents the fact that the scent CD has already been played once (FIGS. 6 and 15). If, however, the sampling pin detects before the playback operation the fact that the scent CD 5 has already been played once and that the scents have already been affected negatively by a possibly advanced aging process, then the playback operation is not started.

The destruction of marking tab 40 need not take place after the first scent is retrieved but instead may preferably be initiated only after a later scent in the motion picture, e.g., the next-to-last scent, to make it possible for a movie that has been viewed incompletely to be watched to the end later with the scent accompaniment.

If a scent CD is to be made so that it can be played back more than once, the release of an additional playback may also be linked to a playback twice or more previously. For example, multiple marking tabs 40 may then be provided in succession or side by side, and they may then be located by suitably modified sampling pins.

Detection and control of the frequency of playback of a disk may also be performed by electronic or other means instead of by mechanical means. Thus, for example, it is feasible to implement this information on a magnetic strip 50 (FIG. 6) on the disk which can be read by the playback apparatus 24 by means of a corresponding magnetic strip reader 70 (FIG. 15).

Since an important aging factor with a scent disk is also due to how much time has elapsed since it was played the first time, the playback limit can also be defined in advance by a certain period of time which is stored as information on the disk and/or the playback apparatus (FIG. 15).

Thus, for example, it is possible to have the playback apparatus impart the time of playback to the disk on the initial playback, e.g., in the form of a mechanical code 53 (FIG. 6), such as a punched card, etc., or a magnetic strip 50 on the disk (FIG. 6) or other equally suitable measures.

The playback time could be relayed by an internal clock or by a signal transmitted together with the scent motion picture.

After this point in time, the disk can still be played for a defined period of time, e.g., for a week. After this period of time has elapsed, the apparatus will refuse to play the disk again. This makes it possible to ensure that despite multiple playing of a disk, the scents used in it are still definitely in a satisfactory condition when the respective motion picture is played.

The length of the possible playback interval may be the same for all disks or it may be associated with the most sensitive of the scents used in the disk.

Such a time limit to playback can also be linked to the minimum stability of the scents used on the disk without any prior playback. Thus, for example, a disk that was sold in March 1997 and whose stored scents would be perfectly stable until approximately December 1999 could be provided with a suitable time code at the time of manufacture, e.g., a mechanical, optical or magnetic time code.

Then if this disk remains unused for a very long period of time and the user does not attempt to play it back until June 1999, when the scents might no longer play back with satisfactory results, the playback apparatus will refuse to play the disk accordingly.

In addition, as an alternative or additionally, it is also possible for the playback apparatus to give the user the information that the disk is already too old instead of just refusing the service.

If it is possible some day to manufacture scent sensors in sufficient quality at reasonable prices, it would also be possible to install such a scent quality sensor directly in the playback apparatus.

Quality assurance of the scents could also be established here simply through quality control of such sensors instead of through a time playback limit of the scent disks.

Since the individual perception of scents has a much greater range of variation than with other sensory stimuli, it has been made possible with the present embodiment in FIG. 6 (in addition to the possibilities of individually influencing the scents through the general scent intensity, temperature, etc. on the playback apparatus as described above) to modify a movie presentation accompanied by scent according to additional particulars of the individual user's presentation (FIG. 15).

First, scents to which a certain number of users could have a specific aversion are classified in scent classes. Then if a user wants to exclude one or more of the scent classes provided from a movie or music presentation, etc., accompanied by scents, he can do this by selecting not to play these scent classes on the playback apparatus or by means of filter codes 55, which may be set on the disk itself. The unwanted scents are then ignored by the playback apparatus and the respective scents are skipped.

If there are users who have a very low opinion of the scent of a perfume, for example, they will set this first with a suitable precode that can be selected on their playback apparatus (e.g., "perf.not" etc.) or by preselectable grids or filter codes 55 on the disk (FIG. 6).

Then when a movie in which a perfume occasionally occurs (e.g., "Pretty Woman," F. Zeffirelli's "Romeo and Juliet" from 1968 or "Gone with the Wind"), the presentation of a perfume will be either omitted entirely or will be presented only in a very attenuated form when the playback apparatus is set accordingly.

For the second form of attenuated scents, a suitable automatic scent attenuator is built into the apparatus and is linked to the incoming signals of the scents that have been rejected.

Such attenuation of scents may be accomplished, for example, by reducing the air flow in the playback apparatus or by an additional admixture of fresh air.

Finally, if another user with different preferences decides to view a movie accompanied by scents, he will set a different personal precode on the playback apparatus accordingly, so that in addition to the above-mentioned individual control of the general scent intensity, a scent movie experience perfectly adapted to the individual user can also be presented.

Precodes that are linked to other properties of the presentation and may also be provided on the scent CD 5 itself are also conceivable.

Thus, for example, it is possible to set the scent CDs themselves for certain characteristics, e.g., nation-specific preferences in scent perception. For example, it is known that the scent of jasmine is much less beloved by Europeans than Asians, and conversely the aroma of pizza is much more appreciated in Europe than it is in Japan, for example.

With a suitable (e.g., nation-specific) precode 53 (FIG. 5) which can be set on the scent CD 5 itself (e.g., by means of a mechanical precode 53 or by a magnetic strip 50, FIG. 6), it is possible, for example, to first produce an internationally standardized CD and then adapt it to specific requirements (e.g., of the distribution region) without any change in production.

A suitable (e.g., nation-specific) specification of the scent presentation can also be accomplished through the signals which are also transmitted with the movie. Thus, for example, transmitter signals originally associated with a scent that is not especially appreciated in a certain country can be either suppressed or attenuated for that country in a suitable signal modification in the transmitter.

In addition, means may also be provided for setting the intensity of an entire scent presentation or other general properties of a presentation (e.g., thermal values or interval profiles) with suitable precodes on the scent disk itself, as proposed above as a setting option for the playback apparatus.

Finally, it is possible by combining the various setting options and precodes to create an individual user profile for each individual user which is then stored on the playback apparatus and can then be retrieved by the user.

Then by operating a single pushbutton, etc., it is possible to retrieve and preset, for example, five different user-oriented precodes, a preferred intensity control, a heat profile, an interval profile and a quantity profile at the same time.

Such a user profile can also be based on additional conditions, e.g., the user's current moods or other characteristics, the seasons of the year, etc. Certain scents are known, for example, to be able to have a positive influence on moods and thus the presentation of one and the same movie could turn out differently for a user who is depressed than one who is elated, for example.

On the whole, this yields at least four types of modification of a movie, music or other presentation accompanied by scents: in general by modification of the transmitter signals or on the disk and individually by settings on the playback apparatus or on the disk.

In the embodiment of the invention illustrated in FIG. 7, the very thin function layers are accommodated in a double scent CD arrangement, if more scents are needed, e.g., for playback of an especially long movie, than can be accommodated on a single disk. In this case, the bottom half 9 of the disk of the top scent CD simultaneously serves as the top half 8 of the bottom disk of the scent CD.

In an especially space-saving modification of this embodiment according to FIG. 7a, no intermediate layers are provided between the two scent layers, but instead the individual scent carrying layers are arranged so that the volumes of the next layer come to lie in the gaps of the preceding layer.

Instead of the two scent carrying layers, it is also possible to use a middle scent carrying layer which is printed with scent strips on both sides, with separating films 12 applied to both scent carrying sides of the middle layer.

The total area needed to accommodate a scent on the scent CD can also be influenced by the intensity of the scent mixture selected as the basis of the encapsulation process. If especially intense mixtures that can be accommodated in a very small space are used, it is also possible with another modification of the embodiment according to FIG. 7 to accommodate the scent carrying slotted channels 3s, which are very narrow in this case, on edge within protective tubes 21s which are likewise very narrow.

The narrow protective tubes 21s here are arranged on edge side by side in the scent CD, which is still very flat, approximately as illustrated in the right portion of the scent CD in FIG. 7.

With the embodiment illustrated in FIG. 8 and possibly other embodiments of the invention (not shown), the scent carrying films and separating films 12 are likewise designed through additional forms and arrangements so that the scents encapsulated between them automatically rupture when air flows through, thus releasing the previously enclosed and preserved scent.

Thus, for example, it is possible to provide the two films 11 and 12, which are glued together along with the scent during the manufacturing process, with various folds and turns (FIG. 8) which are ultimately unfolded and unwounded by the air flowing through, where the scent carrying film 11 and the separating film 12 are also separated from one another and automatically release their scent.

Small scent strips or fibers may also be combined or glued together in a spiral during the manufacturing process in such a way that these small scent carrying spirals unwind and release the scent in presentation of the scent by the carrier medium such as air flowing into the protective tubes 21. In many cases, these may also be scents not enclosed in scent capsules.

With another preferred embodiment of the scent CD shown in FIG. 9, rotation of the S-CD is also avoided for the playback of a respective following new scent. The individual scent tracks 31 are simply arranged side by side here and are played later during playback through separate inlet nozzles.

If it is necessary to apply another scent, although attenuated, of a scent already present, or a scent already used with another scent CD, to a scent track 31 during the manufacturing process, it is possible here to provide only a short length of the scent track with scent tracings, resulting in a modified scent track 32. This avoids having to mix this scent again anew, which can reduce costs during the manufacturing process.

To avoid new mixing work and to reduce the quantity of scents that must be stocked up by the manufacturer of the disks on the whole, it is likewise possible here in the manufacture of a scent CD for a new movie to apply multiple different scents at the same time on a further modified multiple-scent track 36, to produce a newly composed mixed scent from this, if this new mixed scent corresponds to movie director's ideas.

Thus, for example, it is possible to apply a floral scent in the first part 37a of the new multiple-scent track 36 from existing fresh scent ingredients of previously manufactured scent CDs, and to apply a meadow scent in the second part 37b, so that then the impression of the scent of a meadow of flowers is formed from the interaction of the two scents.

With another modified scent track 34 in this embodiment, the scents are applied in such a way that they develop only partially at normal atmospheric pressure. The remaining portions of the scent carrying separating films 12 do not separate until the air pressure increases (e.g., as shown in FIGS. 2b and 4b). Something like that can also be achieved by angling the films in various ways.

Figure 10:
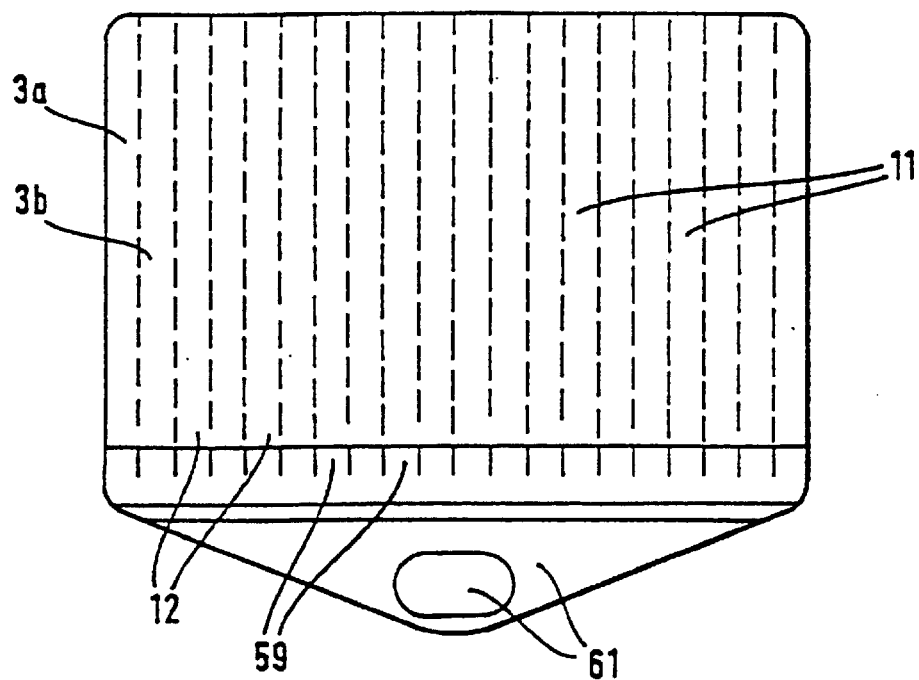
FIG. 10: another embodiment of the scent CD with manual preparation of the possibility of activation.
Figure 11:
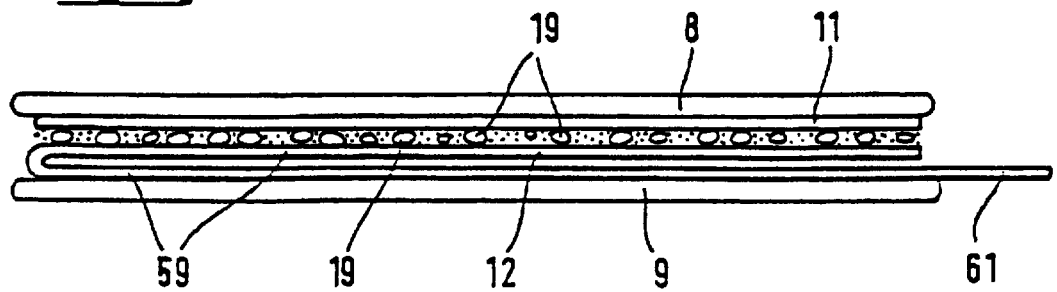
FIG. 11: a longitudinal section through the embodiment from FIG. 10.

In another modification (shown in FIGS. 10 and 11) of the scent compact disk 1 from FIG. 9, the micro scent capsules 19 applied in the slotted channels 3 are activated manually rather than being automatically activated by the detachment of the separating films 12 caused by the penetration of air. The separating films here are connected to each other in a handle-like outside part, the so-called activator 61, in the area of the inlet ports 2.

If a user intends to view a scent-accompanied presentation of a motion picture, he will pull on the activator 61 of the separating films (FIG. 11), with them all being pulled away together from the other scent carrying film, which thus activates them. Next, this activated disk is inserted into the playback apparatus (FIG. 15), whereupon the scents that are activated at the same time do not become mixed or escape to the outside due to the fact that they remain accommodated in the protective tubes.

With this modification of the disk, it is possible to greatly reduce the required air pressure of the playback apparatus because now the air pressure need not be so high that the separating films 12 are automatically detached from the top side 11 of the film, and the scents also remain activated in the scent capsules 19 until shortly before use.

With another modification (not shown) of this embodiment, novel scent carrying applications, so-called scent carrying touch coatings 58 are used on the scent carrying top side 11 of the film, for example. The scent carrying touch coatings 58 are not activated by separating the two films 11 and 12 from each other but instead are activated merely by touching the surface of the touch coatings 58 or by touching an object to it. In this case the touch coatings 58 are preferably applied to one side within the disk, e.g., directly to one or both halves 8 or 9 of the disk, or to one of the scent carrying films 11 or 12. Then an activator 61 is installed in front of the scent carrying parts 11/12/8/9 and is removed manually or automatically before playback by the playback apparatus. The scent carrying parts 11/12/8/9 and the activator 61 together form the scent matrix 60.

By removing the activator 61, the touch coatings 58 in the scent matrix 60 are touched in such a way that the scents in the coating are activated. Immediately thereafter, the activated scents in the scent CD are then retrieved by certain signals and presented by a method essentially similar to that in the embodiments described above.

With other variations of the invention, scent carrying coatings are provided with microencapsulated scents that can be activated by vacuum, light, heat or other triggering means.

Before the scents of such a disk can be played back, the inherent scents are first activated by an appropriate triggering means and prepared for the playback operation.

Thus, for example, light-sensitive scents or light-sensitive seals can be activated by guiding a light source such as a laser beam into the scent tracks before playback.

If such scent tracks are also sealed by inlet and outlet seals 10 and 22, these seals are removed or rendered ineffective before the triggering means such as the laser beam penetrates through them.

With another variation of this embodiment, the disks are shaped in the form of round flat storage media, as illustrated in FIG. 1. In this case, the two halves 8 and 9 of the disk are essentially only partially joined together. The connection of the disk halves is preferably such that the disk halves are not separated from each other but can be rotated against each other about the center axis.

If such a disk is to be activated, the top and bottom halves 8 and 9 of the disk are rotated against each other about the axis for a short distance, whereupon the scent carrying touch coatings 58 inside are activated by the touch of an internal or external triggering means and the disk is thus ready for playback.

In another embodiment of the invention (illustrated in FIGS. 12a and b), for transport, shipping and storage, the scent CD is manufactured to be even flatter than in the previous embodiments by entirely eliminating the possibility of through-flow of air, etc. The displacement cavity 13 shown in FIGS. 2a, b and 4a, b or other cavities that allow air flow past the inherent scents are thus not present to any an extent during transport (FIG. 12a) in this embodiment, so that such a scent CD also approximates more closely the diameter of a music CD or CD-ROM.

If this embodiment of the scent CD is to be played, it is first enlarged by the user before the actual playback or is automatically enlarged by the playback apparatus to a slightly larger volume than its transport volume.

This increase in volume can be accomplished, for example, by providing the top and bottom halves 8 and 9 of the disk with a small catch 35 on the side, so that the user can insert a coin, for example, into this side catch 35 and turn it, so that the scent CD halves 8 and 9 move a small distance away from each other. Due to a small spacer 38, this distance between the halves of the CD is maintained during the playback operation, but the scent CD can also be opened automatically by the playback apparatus.

Figure 12A:
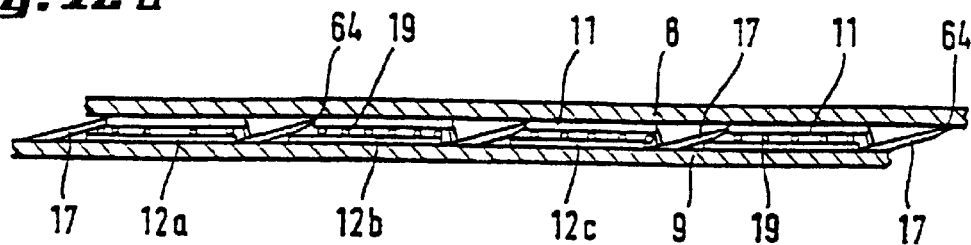
FIG. 12a: another embodiment of the scent CD with minimization for transport
Figure 12B:
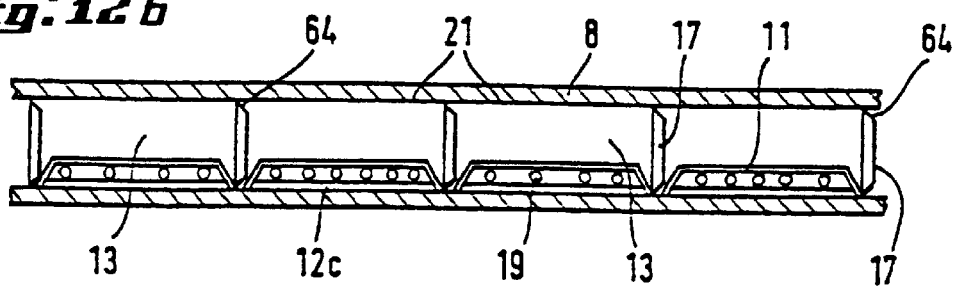
FIG. 12b: the embodiment of the scent CD from FIG. 12a in the unfolded and ready-to-play state.

Only after this opening process is the required space for air or other media to pass over the scents stored on the slotted channels 3 of the scent CD or on other inherent scent contact surfaces (FIG. 12b).

To ensure that airtight tubes are still formed with the definite alignment of the air stream around the slotted channels 3 or other scent carrying surfaces, the previous dividing webs are replaced in this embodiment by modified flexible dividing webs 17 which become aligned without rupturing during the volume-increasing step.

The ends of the flexible dividing webs 17 can be connected to the disk halves 8 and 9, e.g., by plastic hinges 64.

In another modification (shown in FIGS. 13a and 13b) of the embodiment according to FIGS. 12a and 12b, micro scent capsules 19 in the disks are activated simultaneously with the process of opening the top and bottom disk halves 8 and 9, as described with regard to FIGS. 12a and b, by separating the scent carrying films 8 and 9 from each other, at least in the middle area, by the operation of opening the disk.

The oncoming air or other medium need no longer apply the force to separate the scent carrying films 8 and 9 from each other, but instead it can flow unhindered past the scent capsules 19, which have already ruptured.

Figure 13A:
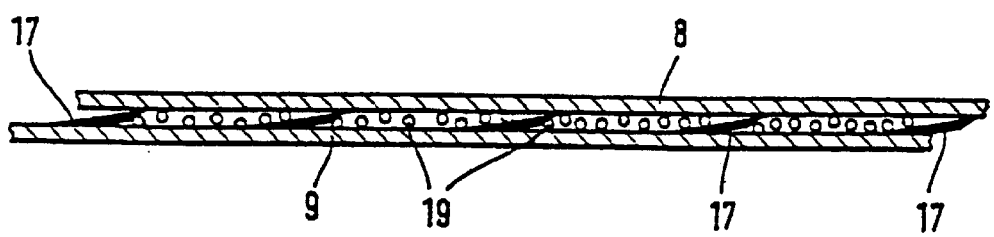
FIG. 13a: another embodiment of the scent CD with transport minimization for in the transport state.

In this case, the micro scent capsules 19 can also preferably be applied in such a way that there is no slotted channel 3, or not a complete slotted channel, or scent carrying films 11 and/or 12 in the protective tube 21 (FIG. 13a).

Finally, the micro scent capsules 19 are applied or glued directly to the top half 8 and/or the bottom half 9 of the disk, with disk halves 8 and 9 ultimately being connected by flexible dividing webs 17 and folded up so that the scent capsules 19 mostly come to lie directly between disk halves 8 and 9 (FIG. 13a).

Figure 13B:
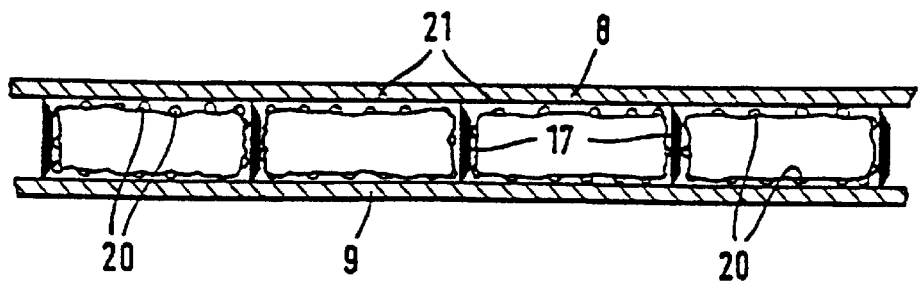
FIG. 13b: the embodiment of the scent CD from FIG. 13a in the activated state.

When disk halves 8 and 9 are opened, the flexible dividing webs 17 lying flatly between them become aligned, with the micro scent capsules 19 glued between them being ruptured, forming ruptured capsules 20, while on the other hand the volume required for the flow of air, etc., in the disk is created with the volume increase achieved simultaneously by opening the disk (FIG. 13b).

With another variation of this embodiment of a disk (not shown), a displacement cavity 13 or other cavities that permit air flow past the scents inside are not yet present as an extent in the transport state or the sealed state. At the same time, this disk variation does not have microencapsulated scents, but instead in this case the scents are applied to the disk by other methods described above to permit a rapid and very short-term production of disks for a certain event by omitting the time-consuming encapsulation procedure.

The greatly inferior preservation options for such disks with unencapsulated scents are partially compensated in this variation of a scent disk by the fact that the cavity 13, which is not yet present in the sealed state, is placed over the scent tracks so closely that this yields a preservation effect (similar to that in the embodiments in FIGS. 12a and b or 13a/b). By largely excluding any type of cavity above the scent tracks, this yields a type of sealing of the scents, so that penetration of oxygen and other substances that would accelerate the aging process is prevented.

If these disks which are intended for short-term use are opened just before playback, the cavities 13 that are necessary to allow sufficient air flow are also formed (approximately as in the modification of the previous embodiment of FIG. 13a according to FIG. 13b).

In another modification (not shown) of the embodiment, little or no internal volume is provided for the flow of air, etc. However, first at least the slotted channels 3 are designed to be entirely or partially elastic, so that first the walls of the slotted channel are expanded in activating of a scent carrying slotted channel 3 to the extent that volume is provided around the channel, in which case the air pumped up to it can flow past scent carrying materials 26, micro scent capsules 19 or other scent reservoirs provided in the disk.

The pressure resulting here in an activated slotted channel 3 is also transmitted to the protective layers (e.g., protective tubes 21) around the slotted channel, so the latter are designed to yield briefly during the activation and thus permit air flow to the required extent. Such an elastic slotted channel may also be used in other embodiments described here.

Finally, with the embodiments described last, it is possible to keep the scents, which require almost no volume, extremely small for transport, whereas in their presentation, the cross sections of air volumes flowing past the scent can be kept large at the same time.

Another embodiment of the invention illustrated in FIG. 14 concerns a variation of the embodiment according to FIG. 6.

For reasons of simpler recycling of the disks that have been played and also to simplify manufacturing, first a plastic hinge 52 is inserted between the ends of the top half 8 and the bottom half 9 of the disk (FIG. 14).

In the manufacture of such a one-piece folding disk 49, the disk halves 8 and 9 need no longer be joined together in an accurate fit, but instead they are already joined and secured to each other by the plastic hinge 52.

The scent carrying films 11 and 12 need only be inserted between disk halves 8 and 9 of folding disk 49 after they have been manufactured and joined, whereupon the disk halves are folded together, securing the scent carrying film layers 11 and 12 inside.

To avoid welding the disk halves 8 and 9 at the upper end of folding disk 49, which welding might be difficult to release, one or more catch projections 57 are provided there to engage when disk halves 8 and 9 are folded together and thus fixedly secure the folding disk in the folded condition. Catch projections 57 are preferably provided on folding disk 49 in such a way that they cannot be opened by the user but instead can be opened only with special equipment.

Since the cuter seal of a folding disk 49 or its protective tubes 21 is not as great as that with a scent CD that has been welded together, the internal scent carrying films 11 and 12 here are preferably designed to be maintained as scent carrying flat channel 33, in which case the air masses flowing past them are carried only through the flat channel and do not require any further sealing by protective tubes 21.

If the disk has finally been played and the internal scent carrying layers 11 and 12 and channels 33 are to be separated from the disk halves as part of recycling, folding disk 49 is then opened by a special device, layers 11 and 12 or 33 or the like are removed and the disk is fitted with new scent carrying films. If, for the purpose of disposal, the protective sheathing or disk halves 8 and 9 are to be disposed of, they can also be recycled after separating the scent carrying films. Accordingly, materials that fulfill the function while also being biodegradable and/or recyclable can be used for disk halves 8 and 9 or for folding disk 49.

In another variation of the embodiment of the invention according to FIG. 14, the connections between the top half 8 of the disk and the bottom half 9 are designed as permanent glued joints, welded joints, etc., despite the folding form. These connections are preferably designed so that they can rupture to remove the scent carrying layers for the purpose of disposal of a disk.

In another embodiment of the invention (not shown), the individual scent carrying films are joined together in succession rather than side by side, thus resulting on the whole in a scent carrying tape on which are located all the scents of an intended presentation. The scent carrying tape likewise consists of a top film and a bottom film between which the scents are stored, preferably in the form of microcapsules.

The length of the scent carrying strips on this tape is standardized, so that a new scent can be located precisely by advancing the two-film tape by a defined length.

If playback of a scent is intended, the two-film tape will advance, controlled by appropriate signals, exactly so far that the strip with the intended scent comes to lie in front of a protective channel.

The scent carrying films of the tape are separated here from each other, so that they are now exposed in the area of the is protective channel and the scent capsules are opened.

The protective channel guides the scented air dispensed from the opened microcapsules to an outlet. A protective channel for the transport of multiple scents or for the scent being played back at the time is provided here.

This modification of storage in the manner of a scent tape is especially suitable if repeated playback of one and the same scent or only a few different scents is provided.

In this form, it is thus preferably a method of preservation for the presentation of a single scent or only a few scents that are to be presented over a longer period of time, each always in a satisfactory form.

With other modifications of this invention (not shown) the scent CD is played, for example, in combination with a music CD player or while a computer game is running.

Other applications are derived inasmuch as the scent CD is to be played by an automatic food or beverage dispenser for passing interested customers, either automatically or in response to a pushbutton. It is possible in this case for the scent CD not to contain different scents but instead 50 applications of the same scent, where the scent CD is used here mainly instead of a large liquid scent container to ensure that the scents presented will be kept fresh optimally, which is not usually possible in the long run with liquid scent supplies that are in constant contact with air (see preceding paragraph).

Finally, such scent CDs, which make it possible for the first time to automatically play back scents of perfect quality and even sets of very different scents at any desired location to accompany certain events and to adjust this individually as needed to conform to the personal perceptions of the consumer or viewer, can be used for a wide variety of different applications.

This is true in particular if the use of scent impressions previously had to be omitted with these applications because scents could in general only be blown into a space, if at all. Thus many consumers who do not particularly appreciate said scent or to whom this scent impression would appear too strong or too weak could be disturbed by this.

A decentralized multiple scent reservoir as proposed in the present invention, which plays back scents in the desired type and quality, can avoid this problem of measuring everything by the same yardstick and permit a pleasant scent experience for each consumer at the location and time and in the manner and intensity personally desired by that consumer.

Various combinations of the embodiments or parts thereof described here are combined in other embodiments of the invention that are not discussed in greater detail here.

What is claimed is:

1. A method for dispensing scent comprising the steps of:
   A) storing scent substances in respective channels which pass through a base body, each channel including an inlet port and an outlet port;
   B) sealing the inlet and outlet ports of each channel with respective elements for sealing each channel against volatization; and
   C) dispensing the scent substance of a selected channel by opening the seal elements thereof and conducting a pressurized stream of gas through the selected channel, the opening of at least one of the seal elements performed by destroying that seal element.

2. The method according to claim 1 wherein the destroying of the at least one seal element in step C is performed by the pressurized gas stream.

3. The method according to claim 1 wherein step A comprises positioning microcapsules in the respective channels, the microcapsules carrying the scent substances.

4. The method according to claim 3 wherein step A further comprises positioning the microcapsules between opposing surfaces of the respective channels and adhesively joining the opposing surfaces of each channel to one another, wherein the microcapsules become adhered to both opposing surfaces, step C comprising forcing the opposing surfaces of the selected channel away from one another by a force of the pressurized gas stream, to cause rupturing of the microcapsules.

5. The method according to claim 1 wherein step A comprises storing different scent substances in respective channels.

6. The method according to claim 1 wherein step C comprises opening both seal elements of the selected channel by destroying those seal elements.

7. A method for dispensing scent comprising the steps of:
   A) storing scent substances in respective channels which pass through a base body by positioning microcapsules in each channel, the microcapsules containing the scent substances; and
   B) dispensing the scent substance of a selected channel by conducting a pressurized gas stream through the selected channel to cause the microcapsules therein to rupture.

8. The method according to claim 7 wherein step A comprises positioning the microcapsules between opposing surfaces in each channel and adhering the microcapsules to both of the opposing surfaces, step B comprising forcing the opposing surfaces of the selected channel apart in response to the passage of the pressurized gas stream therethrough to produce rupturing of the microcapsules.

9. The method according to claim 8 wherein each of the opposing surfaces comprises a film, step A comprising adhering the respective films of each channel together by an adhesive which also joins the microcapsules to the films.

10. The method according to claim 7 wherein step A comprises storing different scent substances in respective ones of the channels.

11. A method for dispensing a scent substances comprising the steps of:
   A) providing a base body having channels passing therethrough, each channel formed by opposing surfaces and including a gas inlet port and a gas outlet port;
   B) attaching a scent substance to at least one wall of each channel; and
   C) passing a pressurized gas flow through a selected channel between the opposing surfaces thereof to cause the scent substance therein to become entrained in the gas flow.

12. The method according to claim 11 further including the step of adhering the opposing surfaces of each channel together prior to step C, step C including separating the opposing surfaces of the selected channel away from each other in response to passing the gas flow through the selected channel.

13. The method according to claim 11 wherein step B comprises attaching scent-containing microcapsules to the at least one wall.

14. The method according to claim 11 wherein step B comprises attaching a scent-containing gel to the at least one wall.

15. The method according to claim 11 wherein step B comprises attaching a scent-containing resin to the at least one wall.

16. A method of releasing scent substances, to be dispensed in the form of a gas, where the substances are microencapsulated to form micro scent capsules and embedded in a carrier material, characterized in that the micro scent capsules embedded in the carrier material are ruptured by the kinetic energy of a gas.

17. A method according to claim 16, characterized in that air is used as the gas.

18. A method according to claim 17, characterized in that helium is mixed with the air.

19. A method according to claim 18, characterized in that 1 to 20 vol % helium is mixed with the air.

* * * * *